(12) United States Patent
Eisner et al.

(10) Patent No.: US 10,406,276 B2
(45) Date of Patent: Sep. 10, 2019

(54) SYSTEM AND METHOD FOR GUIDED REMOVAL FROM AN IN VIVO SUBJECT

(71) Applicants: The General Hospital Corporation, Boston, MA (US); Kalera Medical, Inc., San Diego, CA (US)

(72) Inventors: Brian Howard Eisner, Chestnut Hill, MA (US); Darrin Kent, Murrieta, CA (US); Steve Thompson, San Jacinto, CA (US); Matthew Yurek, San Diego, CA (US)

(73) Assignees: The General Hospital Corporation, Boston, MA (US); Kalera Medical, Inc., San Diego, CA (US)

( * ) Notice: Subject to any disclaimer, the term of this patent is extended or adjusted under 35 U.S.C. 154(b) by 0 days.

(21) Appl. No.: 15/649,581

(22) Filed: Jul. 13, 2017

(65) Prior Publication Data
US 2017/0319776 A1 Nov. 9, 2017

Related U.S. Application Data

(63) Continuation-in-part of application No. 14/774,418, filed as application No. PCT/US2014/026037 on Mar. 13, 2014, now abandoned.
(Continued)

(51) Int. Cl.
*A61B 17/22* (2006.01)
*A61M 3/02* (2006.01)
(Continued)

(52) U.S. Cl.
CPC ....... *A61M 3/0283* (2013.01); *A61B 1/00135* (2013.01); *A61B 1/00154* (2013.01);
(Continued)

(58) Field of Classification Search
CPC .............. A61M 3/0283; A61M 1/0058; A61M 3/0279; A61M 25/09; A61B 1/307;
(Continued)

(56) References Cited

U.S. PATENT DOCUMENTS

| | | | |
|---|---|---|---|
| 3,830,240 A | 8/1974 | Antonevich et al. | |
| 4,802,461 A * | 2/1989 | Cho | A61B 1/0051 600/108 |

(Continued)

FOREIGN PATENT DOCUMENTS

| | | |
|---|---|---|
| CN | 203988361 U | 12/2014 |
| WO | 2010068467 A1 | 6/2010 |

OTHER PUBLICATIONS

Villanueva, et al., Silicone Catheters May Be Superior to Latex Catheters in Difficult Urethral Catheterization After Urethral Dilation, Journal of Endourology, 2011, 25(5):841-844.
(Continued)

*Primary Examiner* — Ryan J. Severson
*Assistant Examiner* — Christian D Knauss
(74) *Attorney, Agent, or Firm* — Quarles & Brady LLP

(57) ABSTRACT

In accordance with some configurations, systems and methods for guided removal from an in vivo subject are provided. In some configurations, a method for removing an object is provided. The method comprising, guiding a flexible tube through a passageway of an in vivo subject, wherein the flexible tube comprises at least a first passageway and a second passageway. Positioning a distal end of the first passageway in proximity to the object. Infusing liquid through the second passageway substantially continuously. Removing the object through the first passageway with at least a portion of the liquid while suction is not being provided.

14 Claims, 27 Drawing Sheets

Related U.S. Application Data

(60) Provisional application No. 61/783,239, filed on Mar. 14, 2013.

(51) Int. Cl.

| | |
|---|---|
| *A61B 1/307* | (2006.01) |
| *A61B 1/00* | (2006.01) |
| *A61M 25/09* | (2006.01) |
| *A61M 39/22* | (2006.01) |
| *A61B 18/26* | (2006.01) |
| *A61M 1/00* | (2006.01) |
| *A61B 17/34* | (2006.01) |
| *A61B 18/00* | (2006.01) |

(52) U.S. Cl.
CPC .............. *A61B 1/307* (2013.01); *A61B 17/22* (2013.01); *A61B 17/3417* (2013.01); *A61B 17/3421* (2013.01); *A61B 18/26* (2013.01); *A61M 1/0064* (2013.01); *A61M 1/0084* (2013.01); *A61M 3/0262* (2013.01); *A61M 3/0295* (2013.01); *A61M 25/09* (2013.01); *A61M 39/22* (2013.01); *A61B 2017/22079* (2013.01); *A61B 2017/22084* (2013.01); *A61B 2017/3445* (2013.01); *A61B 2018/00982* (2013.01); *A61B 2217/005* (2013.01); *A61B 2217/007* (2013.01); *A61B 2218/002* (2013.01); *A61B 2218/007* (2013.01); *A61M 2039/229* (2013.01); *A61M 2210/1082* (2013.01)

(58) Field of Classification Search
CPC .............. A61B 17/22; A61B 17/22031; A61B 2017/22038; A61B 2017/22074; A61B 2017/22079; A61B 2017/22084; A61B 2018/00505; A61B 2018/00511; A61B 2018/00517; A61B 2217/005; A61B 2217/007; A61B 1/00154; A61B 1/012; A61B 1/0135; A61B 18/26; A61B 2018/00982; A61B 2218/002; A61B 2218/007
See application file for complete search history.

(56) References Cited

U.S. PATENT DOCUMENTS

| | | | |
|---|---|---|---|
| 4,874,360 A | | 10/1989 | Goldberg et al. |
| 5,476,450 A | * | 12/1995 | Ruggio ................. A61B 17/22 604/104 |
| 5,827,229 A | | 10/1998 | Auth et al. |
| 6,997,867 B2 | * | 2/2006 | Soble ................. A61B 1/005 600/121 |
| 7,540,868 B2 | | 6/2009 | Elliott et al. |
| 7,654,989 B2 | | 2/2010 | Knapp |
| 7,883,515 B2 | | 2/2011 | Kear |
| 8,192,500 B2 | | 6/2012 | Chung |
| 8,597,261 B2 | | 12/2013 | Knapp |
| 8,672,928 B2 | | 3/2014 | Liu et al. |
| D715,921 S | | 10/2014 | Wan |
| 8,858,569 B2 | | 10/2014 | Wan |
| 8,911,415 B2 | | 12/2014 | Knapp |
| 9,295,811 B2 | | 3/2016 | Knapp |
| 2003/0199986 A1 | | 10/2003 | McWeeney et al. |
| 2003/0216760 A1 | | 11/2003 | Welch et al. |
| 2004/0019358 A1 | | 1/2004 | Kear |
| 2004/0153095 A1 | | 8/2004 | Seddon |
| 2004/0267213 A1 | * | 12/2004 | Knapp ................. A61B 1/307 604/284 |
| 2005/0143678 A1 | * | 6/2005 | Schwarz .......... A61B 17/12022 601/4 |
| 2005/0149201 A1 | | 7/2005 | McWeeney et al. |
| 2006/0069343 A1 | * | 3/2006 | Rontal ................. A61B 17/22 604/20 |
| 2007/0298069 A1 | | 12/2007 | Bucay-Couto et al. |
| 2008/0004578 A1 | | 1/2008 | Hixon et al. |
| 2009/0163846 A1 | | 6/2009 | Aklog et al. |
| 2010/0137846 A1 | | 6/2010 | Desai et al. |
| 2010/0305475 A1 | | 12/2010 | Hinchliffe et al. |
| 2011/0060315 A1 | | 3/2011 | Windheuser et al. |
| 2011/0224489 A1 | * | 9/2011 | Deal ................. A61B 17/22032 600/116 |
| 2011/0245841 A1 | | 10/2011 | Shohat et al. |
| 2013/0024003 A1 | | 1/2013 | McWeeney et al. |
| 2013/0165944 A1 | | 6/2013 | Gal et al. |
| 2016/0001050 A1 | | 1/2016 | Yee et al. |
| 2016/0120557 A1 | * | 5/2016 | Goddard ................. A61B 17/22 606/127 |
| 2017/0215899 A1 | | 8/2017 | Harrah et al. |
| 2017/0215964 A1 | | 8/2017 | Harrah et al. |
| 2017/0215965 A1 | | 8/2017 | Harrah et al. |

OTHER PUBLICATIONS

PCT International Search Report and Written Opinion, PCT/US2014/025321, dated Jul. 18, 2014.
PCT International Search Report and Written Opinion, PCT/US2014/026037, dated Sep. 16, 2014.
European Patent Office, Extended European Search Report, Application No. 14775184.6, dated Nov. 17, 2016.
European Patent Office, Extended European Search Report, Application No. 18205890.9, dated Jan. 29, 2019, 5 pages.

* cited by examiner

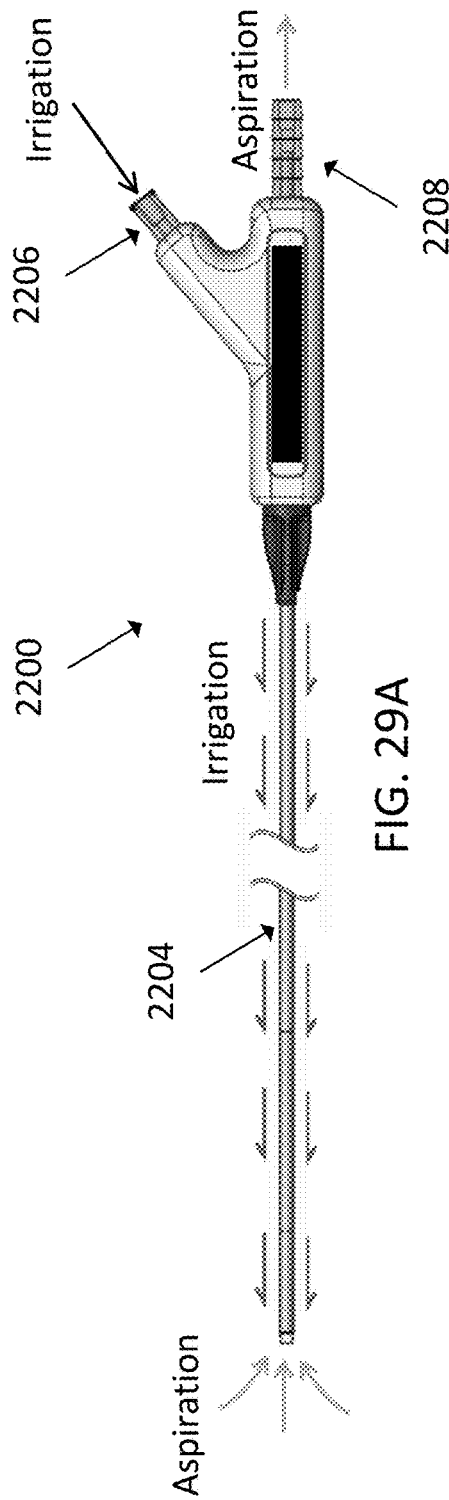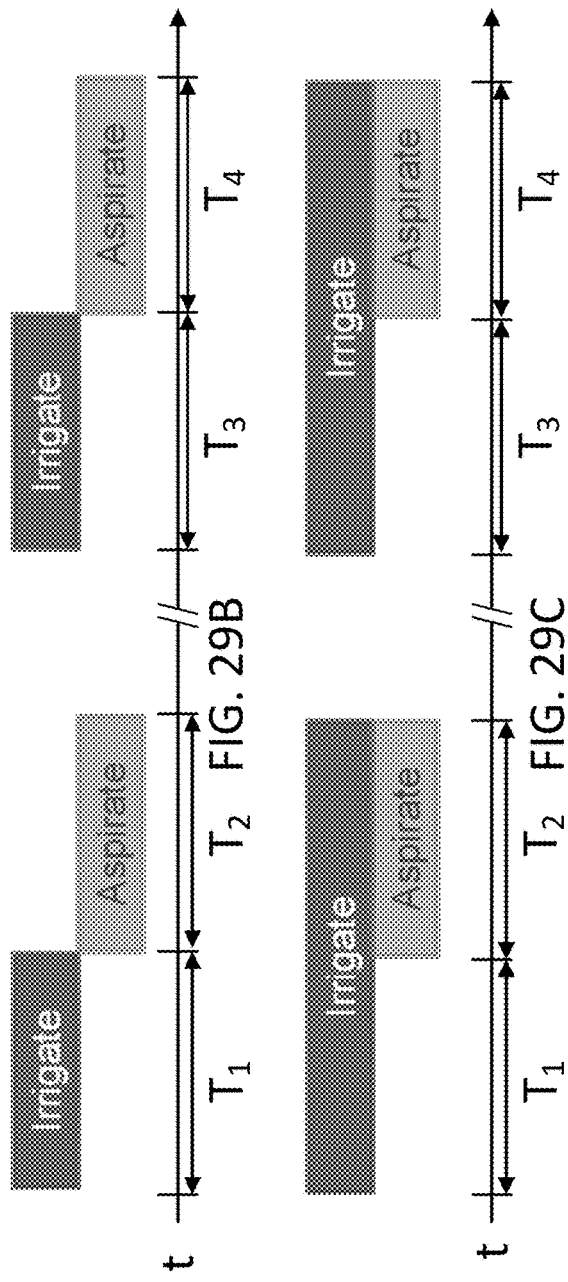
FIG. 29A
FIG. 29B
FIG. 29C

SYSTEM AND METHOD FOR GUIDED REMOVAL FROM AN IN VIVO SUBJECT

CROSS-REFERENCE TO RELATED APPLICATIONS

This application is a continuation-in-part, under 35 U.S.C. § 120, of U.S. application Ser. No. 14/774,418, filed Sep. 10, 2015, which is a National Stage, under 35 U.S.C. § 371, of International Application No. PCT/US2014/026037, filed Mar. 13, 2014, which claims the benefit, under 35 U.S.C. § 119, of U.S. Provisional Application No. 61/783,239, filed Mar. 14, 2013. Each of the foregoing applications is hereby incorporated herein by reference in its entirety for all purposes.

BACKGROUND OF THE INVENTION

The present invention relates to systems and methods for the guided removal of objects in vivo. In particular, the invention is directed to a removal device adapted to traverse compact areas utilizing a navigation mechanism, and more specifically, to capture and/or remove debris through a vacuum tube that is in communication with a suction source.

Kidney stones are a common medical problem that negatively impact millions of individuals worldwide. Kidney stones include one or more solid masses of material that are usually made of crystals and form in parts of the urinary tract including in the ureter, the kidney, and/or the bladder of the individual. Kidney stones range in size from smaller (less than about 1 cm) to very large (more than 4 cm) and may cause significant pain to the individual and damage to the kidney. The overwhelming majority of stones that are treated by surgeons are less than 1 cm.

The recommended treatment for removal of the kidney stones varies according to numerous factors including the size of the kidney stones, the number of kidney stones, and the location of the kidney stones. The most common treatments for kidney stones are shock wave lithotripsy (ultrasound waves used to fracture the stones), ureteroscopy (fracture and removal of the stones using an endoscope that is introduced through the bladder), and percutaneous nephrolithotomy (fracture and removal of the stones using an endoscope that is introduced through a sheath placed through the patient's back into the kidney).

The largest kidney stones are usually removed through percutaneous nephrolithotomy or nephrolithotripsy, or through other similar procedures. In these procedures, a small incision is made through the patient's back adjacent the kidney and a sheath is passed into the kidney to accommodate a larger endoscope used to fracture and remove stones. The stone may be removed directly through the tube or may be broken up into small fragments while still in the patient's body and then removed via a vacuum or other known methods (nephrolithotripsy).

There are numerous drawbacks associated with nephrolithotomy, nephrolithotripsy, and other invasive surgeries requiring an incision in the skin. Namely, such surgical techniques may require significantly more anesthesia administered to the patient, the surgeries are more complicated and pose a higher risk of infection and complications for the patient, and the surgeries require a substantial incision in the patient, which may leave a scar. Additionally, given the invasiveness of the procedure, percutaneous procedures are usually not preferred for smaller kidney stones (e.g., less than 1 cm) depending on the size and location of the stones.

In contrast, traditionally, smaller kidney stones have been treated using other, less invasive techniques including through ureteroscopy. In ureteroscopy, the surgeon typically inserts a ureteroscope into the urethra through the bladder and the ureter to provide the surgeon with a direct visualization of the kidney stone(s) which may reside in the ureter or kidney. The surgeon then removes the kidney stone directly using a basketing device if the kidney stone is small enough to pass through the urinary tract without difficulty, or the surgeon fractures the kidney stone into smaller pieces using a laser or other breaking device. After breaking the kidney stone into smaller pieces, the surgeon removes the laser or breaking device and inserts a basket or other object to capture the kidney stone fragments. Upon retrieving some of the kidney stone fragments, the surgeon removes the basket from the patient and empties the kidney stone fragments therefrom. This process is repeated until clinically significant kidney stones and kidney stone fragments are broken up and removed from the body.

It should be apparent that this process is extremely time consuming, costly, and inefficient because the surgeon is required to insert and remove the scope and basket into and out of the patient many times to completely remove the kidney stones and kidney stone fragments therefrom. Using a basket removal device to capture kidney stones or kidney stone fragments suffers from other drawbacks in that the basket is difficult to position adjacent the kidney stone fragments and maneuver in a manner that effectively retrieves the fragments. The training required for such a procedure is not insignificant and the aforementioned basket removal technique is difficult for even the most skilled surgeons. Additionally, the surgeon is susceptible to hand fatigue due to the extended amount of time required to operate the kidney stone retrieval baskets. Further, the patient is required to be under local anesthesia and/or remain immobile over an extended amount of time. Still further, the basket retrieval devices cause irritation to the urinary tract due to the repeated insertion and removal therefrom.

Other kidney stone removal techniques may utilize suction devices to remove kidney stones and kidney stone fragments from the patient. Such techniques use a flexible tube designed to be disposed within a working channel of a ureteroscope. The flexible tube is designed to have a diameter of between 2 French and 3 French and includes a suction source therethrough. Utilization of this type of device necessarily restricts the size of the passageway available to remove kidney stones and portions thereof from the patient. Indeed, the diameter of the ureteroscope occupies a significant portion of the limited passageway into the patient. Therefore, the size of the flexible tube is bounded by the size of the working channel of the ureteroscope and is defined by a diameter of under about 3 French. The utilization of the working channel of a ureteroscope or other viewing instrument has heretofor been utilized to assist the surgeon in locating the matter to be removed from the patient and to assist in guiding the removal instruments to an appropriate location. The use of these devices is necessarily restricted to removal of debris that is smaller than the size of the tube disposed in the working channel (i.e., under about 3 French). Accordingly, the prior art devices of this type are unable to remove debris greater than about 2 mm and removal of even smaller stones becomes problematic given the narrow lumen size in the prior art devices and their resulting propensity to clog, even with stones of 1 mm or less.

Kidney stone removal techniques may also make use of irrigation systems, devices, and methods to remove stone fragments from the patient. Irrigation is often used during a ureteroscope procedure.

For example, some prior-art devices use irrigation to introduce a liquid, such as water or saline solution, into the kidney. Such irrigation can be used to perform a cleansing that washes very small particles out of the remote interior regions of the kidney. However, any liquid that is introduced must drain from the kidney both during and after the procedure. Therefore, the volume of liquid that can be introduced is necessarily limited, and there is no strong liquid flow to remove fragments that are wetted by the liquid from the kidney. A more effective irrigation procedure is needed to rapidly and reliably remove particles, fragments and debris from the kidney.

A stent may be introduced following removal of stones from a kidney. A retrograde Pyelogram contrast study can be used to both verify that all clinically-relevant fragments have been removed, and to evaluate the extent of injury to the urinary collecting system. In particular, a contrast study provides information on the extent of extravasation of blood and other bodily fluids, which is indicative of the extent of injury. Information gained from a contrast study is useful in making decisions on where to place a stent and how long to leave it in place.

Thus, to further facilitate adoption of new systems, methods, and devices for kidney stone removal, it is desirable to ensure compatibility with stent placement. Placement of a stent after the removal procedure results in improved drainage and accelerated healing. It is not uncommon for edema of the ureter to occur post-procedure, resulting in significant pain. Improving drainage through placement of a stent can reduce the extent of such edema and associated pain. Furthermore, studies show that dilation of the ureter by a stent contributes to more rapid healing. For these reasons, a stent is used in the majority of such procedures worldwide, and in the overwhelming majority of stone removal procedures in the United States. Accordingly, new methods and devices that address the removal of debris greater than about 3 mm and are compatible with stent placement are desirable.

SUMMARY

In accordance with some configurations of the disclosed subject matter, methods for removing an object through a passageway of an in vivo subject are provided.

In accordance with some configurations, a method for removing an object through a passageway of an in vivo subject is provided, the method comprising: inserting a ureteroscope into the passageway; positioning the ureteroscope adjacent to an object to break the object into fragments; removing the ureteroscope from the passageway; guiding a multi-lumen catheter into the passageway adjacent to the fragments of the object using a fluoroscopic imaging device and a guide wire; opening a valve to apply suction to remove at least a portion of the fragments; removing the multi-lumen catheter from the passageway; placing a stent in the passageway; and removing the guide wire from the passageway.

In some configurations, the method further comprises re-inserting the ureteroscope following removal of multi-lumen catheter to confirm removal of the fragments.

In some configurations, re-inserting the ureteroscope following removal of multi-lumen catheter is performed prior to placing the stent.

In some configurations, the method further comprises injecting an irrigation fluid along a first lumen in the multi-lumen catheter and simultaneously or intermittently providing suction through a second lumen in the multi-lumen catheter to remove the fluid and debris along the second lumen.

In some configurations, the method further comprises injecting an irrigation fluid along a first lumen in the multi-lumen catheter by first closing the suction valve and introducing a controlled amount of fluid, then opening the valve to provide suction through the first lumen to remove the fluid and debris.

In some configurations, a first lumen of the multi-lumen catheter has a diameter between 0.5 Fr to 8 Fr.

In some configurations, a second lumen of the multi-lumen catheter has a diameter between 3 Fr to 30 Fr.

In some configurations, the object is a kidney stone.

In some configurations, the passageway is accessed laparoscopically or arthroscopically.

In some configurations, the object is diseased tissue and the passageway is located in an organ or an orifice of an in vivo subject.

In some configurations, the object includes a bladder stone or percutaneous stone.

In accordance with some configurations of the disclosed subject matter, a method for removing an object from a passageway within an in vivo subject is provided, the method comprising: inserting a guide wire along the passageway; positioning a sheath over the guide wire; inserting a ureteroscope into the passageway; positioning the ureteroscope adjacent to an object to break the object into fragments; removing the ureteroscope from the sheath; guiding a multi-lumen catheter into the passageway adjacent to the fragments of the object using fluoroscopic imaging and a guide wire; opening a valve to apply suction to remove fragments; removing the multi-lumen catheter from the passageway; placing a stent in the passageway; and removing the guide wire from the passageway.

In some configurations, the method further comprises re-inserting the ureteroscope following removal of multi-lumen catheter to inspect fragment removal.

In some configurations, the method further comprises re-inserting the ureteroscope following removal of multi-lumen catheter and prior to placing the stent to inspect fragment removal.

In some configurations, the method further comprises injecting an irrigation fluid along a first lumen in the multi-lumen catheter, while simultaneously or intermittently providing suction to remove the fluid and fragments along a second lumen.

In some configurations, the method further comprises injecting an irrigation fluid along a first lumen in the multi-lumen catheter by closing the suction valve, then opening the valve to provide suction to remove the fluid and fragments along a second lumen in the multi-lumen catheter.

In some configurations, the object is a kidney stone.

In some configurations, the passageway is a urinary tract of a human.

In some configurations, at least one of the fragments of the object is at least a portion of a kidney stone having a diameter less than 3.3 mm.

In some configurations, the object is bladder stone or percutaneous stone.

BRIEF DESCRIPTION OF THE DRAWINGS

FIG. 29A is an example of a removal device having ports for irrigation fluid and suction in accordance with some configurations.

FIG. 29B is a timing diagram showing an example of sequential irrigation and aspiration in accordance with some configurations.

FIG. 29C is a timing diagram showing an example of simultaneous irrigation and aspiration in accordance with some configurations.

DETAILED DESCRIPTION OF THE INVENTION

Figure 1:
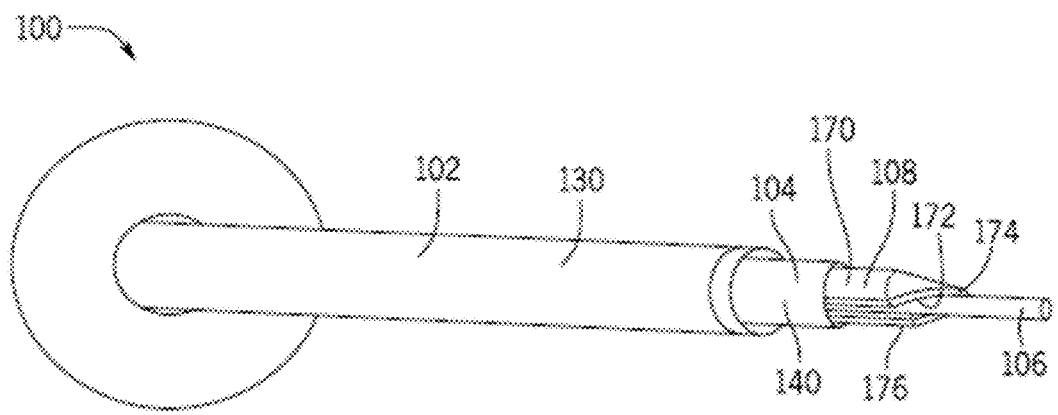
FIG. 1 is an isometric view of a removal device including a sheath, a vacuum tube, an introducer, and a navigation mechanism.

Referring generally to FIGS. 1-8, a removal device 100 includes a sheath 102, a vacuum tube 104, and a navigation mechanism 106. The removal device 100 optionally includes an introducer core 108 adapted to assist in positioning one or more portions of the removal device 100 in a passageway. The removal device 100 further optionally includes a valve 110 that is in communication with, and assists in controlling suction that is supplied to the vacuum tube 104. One or more of the sheath 102, navigation mechanism 106, and/or introducer core 108 may be optional for use with the removal device 100. For example, in one configuration, the sheath 102 is omitted from the removal device 100.

Figure 7:
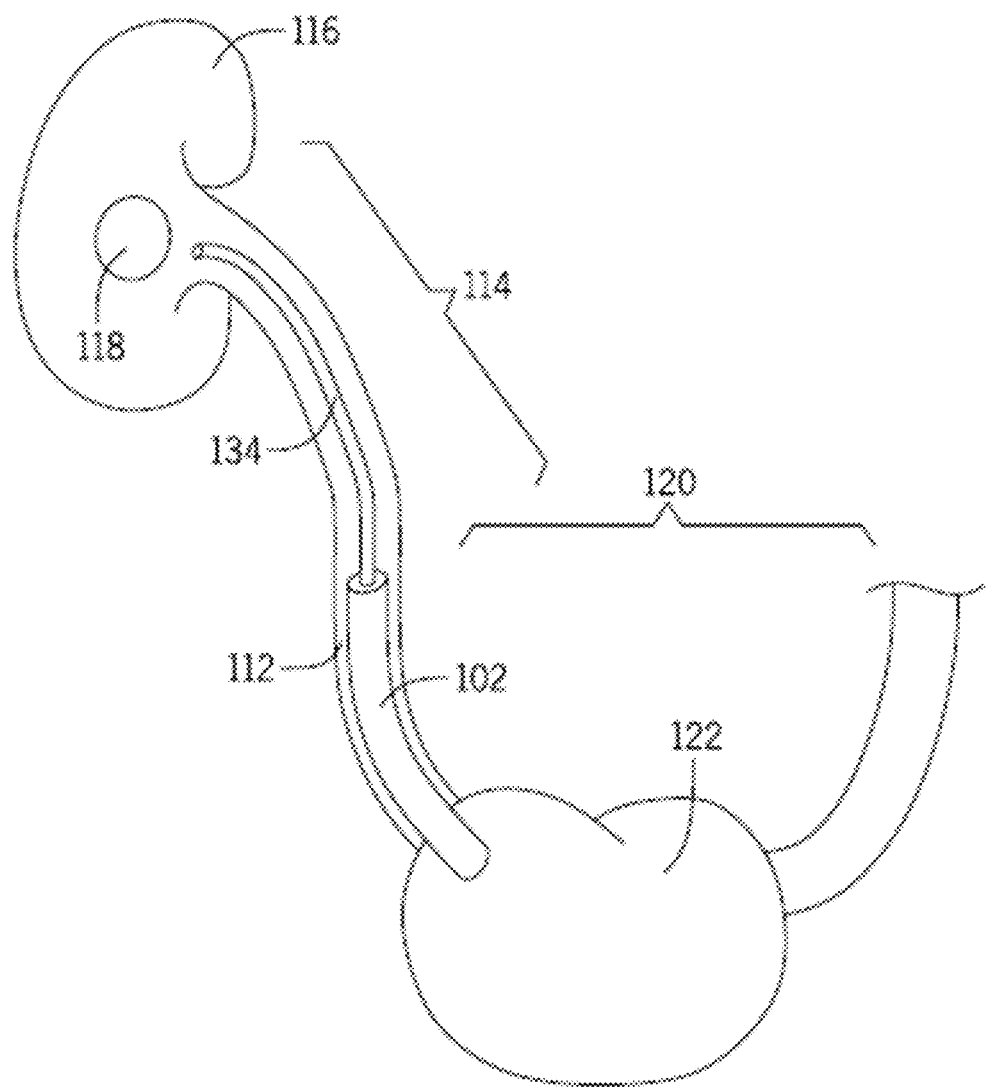
FIG. 7 is a partial schematic view depicting a possible installation of a removal device in a urinary tract of a patient in a first state, wherein a ureteroscope is disposed in the sheath of FIG. 1 adjacent a kidney stone.
Figure 8:
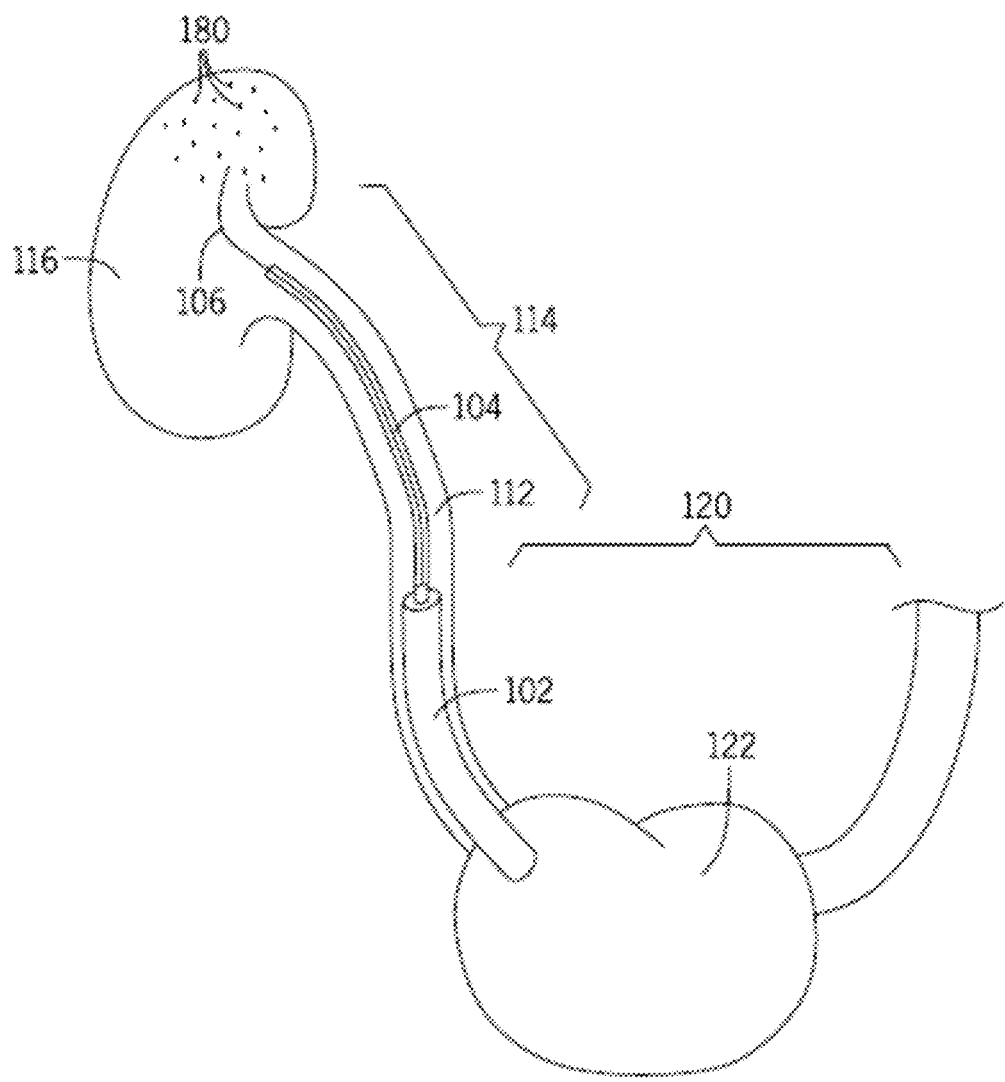
FIG. 8 is a partial schematic view of the removal device of FIG. 7 in a second state, wherein the vacuum tube and navigation mechanism of FIG. 1 is disposed adjacent kidney stone fragments.

As best seen in FIGS. 7 and 8, the removal device 100 is designed to be positioned in a passageway of a patient (e.g., urinary tract), and in particular, into a patient's ureter 112. The removal device 100 includes a renal end 114 designed to be positioned proximate the patient's kidney 116, and more particularly, adjacent to one or more kidney stones 118. The removal device 100 includes a bladder end 120 that is designed to extend through the bladder 122 and out of the patient through the urethra (not shown). The removal device 100 provides an uninterrupted passageway from the kidney stones 118 or kidney stone fragments in the kidney 116, through the ureter 112 and bladder 122, and out of the patient.

Figure 2:
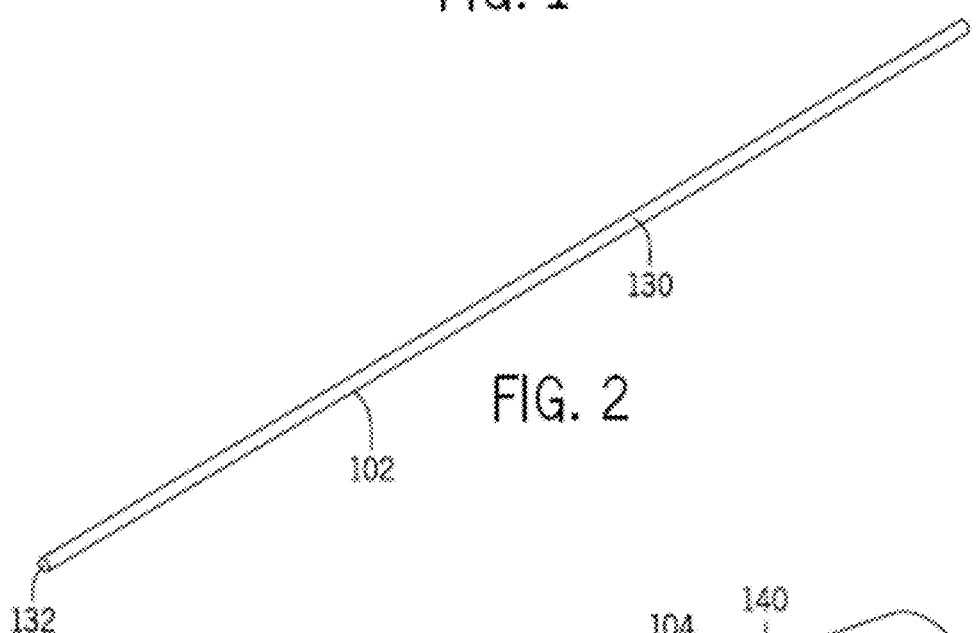
FIG. 2 is an isometric view of a sheath of the removal device of FIG. 1.

Now turning to FIGS. 1 and 2, the sheath 102 is provided as at least one substantially cylindrical tube 130 defining a lumen. The tube 130 includes at least one passageway 132 extending substantially longitudinally therethrough, although additional passageways may be included in the sheath 102 as desired. The passageway 132 extends through the entirety of the sheath 102 and is adapted to receive a ureteroscope 134 (see FIG. 7) and/or other viewing instrument. The ureteroscope 134 preferably includes a laser (not shown) or other mechanism that fractures the kidney stone 118 into smaller fragments (or dust). The passageway 132 is also designed to accommodate the vacuum tube 104 and/or navigation mechanism 106 therein, as described in more detail hereinbelow. The tube 130 is preferably substantially cylindrical to conform to the orifice and/or passageway of the patient in which the removal device 100 is designed to be utilized. In other configurations, the tube 130 includes other shapes as desired. It should also be noted that the sheath 102 may be omitted from the removal device 100 altogether such that the vacuum tube 104 is utilized and serves the function of the sheath 102, which is discussed hereinbelow.

The sheath 102 is preferably made of a biocompatible material that is rigid enough to support the other components of the removal device 100 (e.g., the vacuum tube 104 and navigation mechanism 106), but elastic enough to conform to the contours of the passageway of the patient. For example, suitable materials for use as the sheath 102 include polymers and copolymers such as polyurethane, polyvinyl chloride, polyethylene, polypropylene, and polyamides. Other useful materials include other biocompatible plastics, e.g., polyester, nylon based biocompatible polymers, polytetrafluoroethylene polymers, silicone polymers, and other thermoplastic polymers.

The sheath 102 is preferably defined by a length dimension of about 15 cm to about 45 cm. In a different configuration, the sheath 102 includes a length dimension of about 20 cm to about 35 cm. In a further configuration, the sheath 102 has a length dimension of about 25 cm to about 30 cm. It should be apparent that the length of the sheath 102 may be adjusted in view of numerous factors including, for example, patient size.

The sheath 102 is further defined by an interior diameter dimension of the tube 130. In one configuration, the interior diameter of the tube 130 is between about 2 Fr. to about 30 Fr. In a different configuration, the interior diameter of the tube 130 is between about 10 Fr. to about 16 Fr. In another configuration, the interior diameter is between about 12 Fr. to about 14 Fr.

Figure 3:
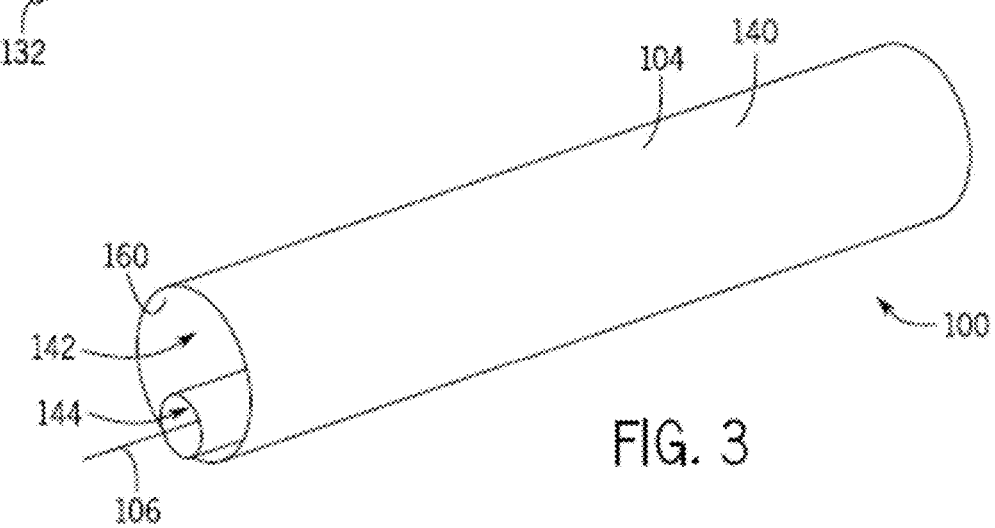
FIG. 3 is an isometric view of the vacuum tube and navigation mechanism of FIG. 1.
Figure 4:
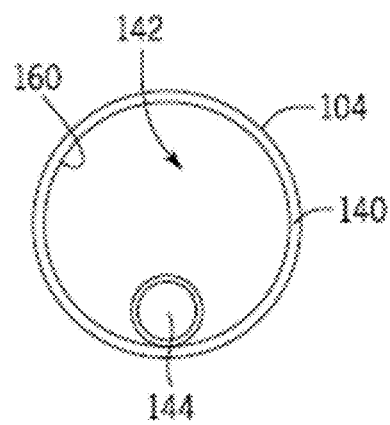
FIG. 4 is a front elevational view of the vacuum tube of FIG. 3, with the navigation mechanism removed therefrom for clarity.

Now turning to FIGS. 3 and 4, the vacuum tube 104 is characterized by an elongate dual lumen 140 defined by a first (larger) passageway 142 and a second (smaller) passageway 144 extending longitudinally therethrough. The vacuum tube 104 may optionally include a specialized tip (not shown) at an end thereof that assists in maintaining the patency of the vacuum tube 104. The tip may also allow the vacuum tube 104 to be positioned in areas that are difficult to access (e.g., the lowest part of the kidney).

The first passageway 142 is designed to accommodate the introducer 108, which is used to assist in positioning one or more portions of the removal device 100 in the patient, as explained in more detail hereinbelow. The first passageway 142 is also designed to accommodate the suction provided from a suction source 148 (see FIG. 6) that is utilized with the removal device 100. The first passageway 142 of the vacuum tube 104 guides the suction to an area adjacent the kidney stones 118 (and/or kidney stone fragments) and facilitates the kidney stones 118 being removed therethrough. The first passageway 142 acts as a primary passageway for removal of the kidney stones 118 (and/or kidney stone fragments).

Still referring to FIGS. 3 and 4, the second passageway 144 of the vacuum tube 104 is disposed adjacent an internal surface 160 of the lumen 140 and is designed to accommodate the navigation mechanism 106 as shown in FIG. 3. In a different configuration, the second passageway 144 may also accommodate a ureteroscope or other viewing instrument. In still a further configuration, the second passageway 144 may accommodate other devices that may be utilized in conjunction with the removal device. For example, in one particular configuration, a miniature camera, ureteroscope, or other visualization device may be utilized through either the first or second passageway 142, 144. Although depicted adjacent the internal surface 160, the second passageway 144 may be disposed in any other location within the vacuum tube 104, or may be omitted all together. Further, the size of the first and second passageways 142, 144 may be adjusted as desired.

In a different configuration, the removal device 100 and/or vacuum tube 104 includes additional lumens extending therethrough. For example, in one configuration, the removal device 100 includes a first passageway adapted to receive a suction source, a second passageway adapted to receive a camera or other visual aid, and a third passageway adapted to receive a guidewire.

The vacuum tube 104 is preferably made of a flexible biocompatible material such that the vacuum tube 104 is able to move through the contours of the passageway of the patient. The vacuum tube 104 is preferably made of a material that is not susceptible to kinks and knots during insertion, use, and removal. For example, in some configurations, the vacuum tube 104 is constructed of a thermoplastic elastomer, or a natural or synthetic polymer such as silicone. In other configurations, suitable materials for use include other polymers and copolymers such as polyurethane, polyvinyl chloride, polyethylene, polypropylene, and polyamides. Other useful materials include other biocompatible plastics, e.g., polyester, nylon based biocompatible polymers, polytetrafluoroethylene polymers, silicone polymers, and other thermoplastic polymers.

One or more portions of the vacuum tube 104 may include a coating and/or may comprise a hydrophilic or hydrophobic material. The coating may assist in positioning the vacuum tube 104 within the sheath 102, positioning the navigation mechanism 106 within the vacuum tube 104, and/or assisting in debris removal through the first passageway 142.

The vacuum tube 104 may also include a reinforcement mechanism (not shown) along a portion (or all) thereof that assists in maintaining the patency and the flexibility thereof. In one configuration, the reinforcement mechanism is provided in the form of a spiral or non-spiral wire. In a different configuration, the reinforcement mechanism is provided in other forms as known in the art.

In one configuration, the vacuum tube 104 includes a hydrophilic or hydrophobic coating and the vacuum tube 104 is used without the sheath 102. In a different configuration, the vacuum tube 104 is designed to be disposed at least partially within the sheath 102 during use. Therefore, the circumference of the vacuum tube 104 is smaller than that of the sheath 102. The lumen 140 of the vacuum tube 104 is defined by a diameter of between about 3 Fr. to about 30 Fr., more preferably between about 10 Fr. to about 18 Fr., and most preferably between about 11 Fr. to about 13 Fr. In one configuration, the lumen 140 of the vacuum tube 104 is about 10 Fr. In a different configuration, the lumen 140 of the vacuum tube 104 is about 11 Fr. In still a different configuration, the lumen 140 of the vacuum tube 104 is about 12 Fr.

The diameter of the second passageway 144 of the vacuum tube 104 is smaller than the diameter of the lumen 140 and is characterized by a diameter of between about 0.5 Fr. to about 8 Fr., and more preferably between about 3 Fr. to about 6 Fr. In one configuration, the second passageway 144 of the vacuum tube 104 is about 3 Fr. In a different configuration, the second passageway 144 of the vacuum tube 104 is about 4 Fr. In still a different configuration, the first passageway 144 of the vacuum tube 104 is about 7 Fr.

Still referring to FIG. 3, as discussed previously, the second passageway 144 of the vacuum tube 104 is designed to accommodate the navigation mechanism 106 as shown in FIG. 3. The navigation mechanism 106 is preferably provided in the form of a guidewire. Guidewires suitable for use in the removal device 100 are characterized by a diameter of between about 0.014 in. to about 1 in. In one configuration, the guidewire is characterized by an elongate flexible material having a diameter of about 0.035 in. or about 0.038 in. Guidewires suitable for use with the removal device 100 include, for example, the Sensor™ guidewire provided by Boston Scientific (Natick, Mass.), or the Glidewire™ provided by Terumo International Systems (Tokyo, Japan). Additionally, the removal device 100 may be utilized in conjunction with the guidewire described in U.S. patent application Ser. No. 12/660,891, filed on Mar. 5, 2010, and incorporated by reference in its entirety. In other configurations, the navigation mechanism 106 may comprise other devices or mechanisms that assist in positioning portions of the removal device 100.

The vacuum tube 104 and/or other portions of the removal device 100 may be controlled using various control mechanisms. For example, in one configuration, the vacuum tube 104 is controlled using a knob, a lever, a button, a foot pedal, combinations thereof, and the like. Various operational parameters may be controlled with the aforementioned control mechanisms including positioning and/or navigating one or more components of the vacuum tube 104, and/or controlling (e.g., increasing or decreasing) the level of suction.

In one configuration, the guidewire is designed to be inserted into the patient and navigated to the kidney 116. The removal device 100 is passed over the guidewire through one of the passageways described herein (e.g., the second passageway 144). In some instances, the sheath 102 is optionally inserted into the patient first, followed by one or more of the guidewire and/or removal device 100.

In a different configuration, the removal device 100 is designed to interact with and pass over the guidewire. In one configuration, the guidewire is inserted into the sheath 102. In a different configuration, the guidewire is inserted into a portion of the vacuum tube 104 (e.g., through the first or second passageway 142, 144, respectively). The guidewire may be utilized in one or more of the passageways in the removal device 100. In a preferred configuration, the guidewire is initially inserted into the flexible tube 130 of the sheath 102 in conjunction with the ureteroscope 134. The guidewire is also preferably utilized in conjunction with the second passageway 144 as a guidance mechanism for the vacuum tube 104 as described in more detail hereinbelow.

Figure 5:
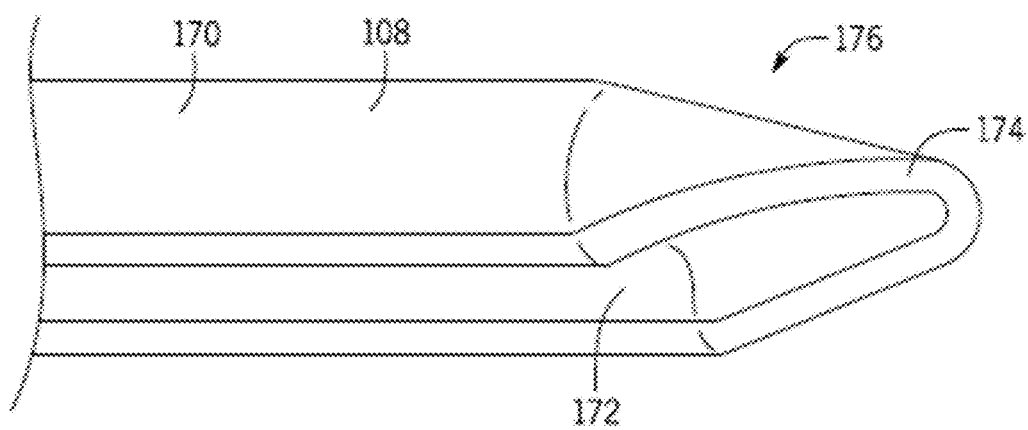
FIG. 5 is a partial isometric view of the introducer of the removal device of FIG. 1 enlarged for magnification purposes.
Figure 6:
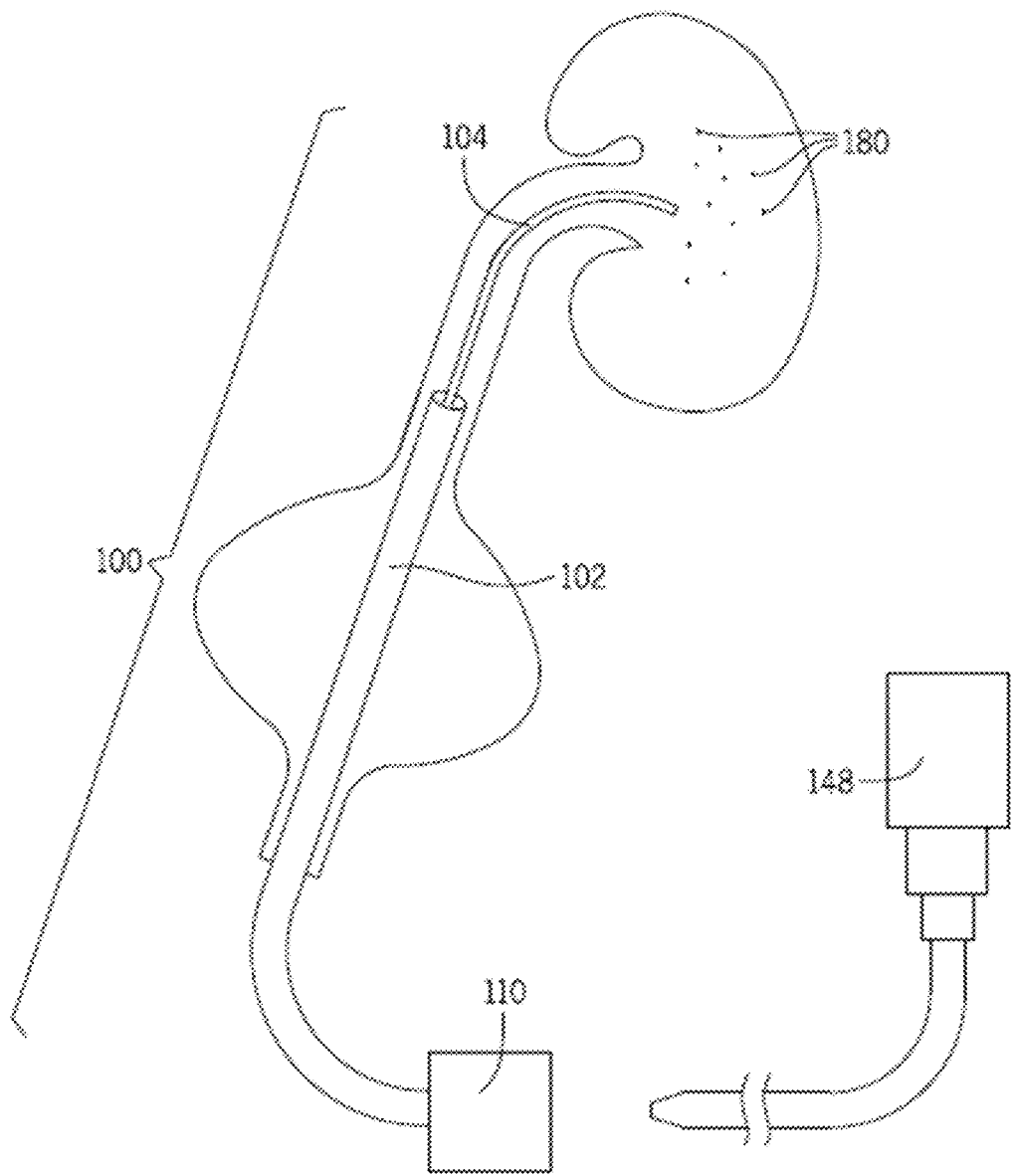
FIG. 6 is a partial schematic view of the removal device of FIG. 1 further including a valve that is in communication with a suction source.

Now turning to FIG. 5, portions of the removal device 100 may optionally be positioned in the passageway with the assistance of a positioning device, for example, such as an introducer core 108. The introducer core 108 includes a rigid, elongate body 170 with a rounded groove 172 extending longitudinally therethrough. The groove 172 preferably has a contour that accommodates the navigation mechanism 106 (e.g., guidewire). For example, in one configuration, the groove 172 is preferably rounded to accommodate a substantially cylindrical guidewire.

The body 170 of the introducer core 108 terminates at a tapered tip 174 at an end 176 thereof. The tip 174 includes a taper that allows the introducer core 108 to be more easily inserted into the patient (i.e., through the patient's urethra). The introducer core 108 is adapted to be disposed in at least one of the passageways of the removal device 100 to provide support thereto. In one configuration, the introducer core 108 is inserted into the sheath 102. In a different configuration, the introducer core 108 is inserted into a portion of the vacuum tube 104 (e.g., through the first or second passageway 142, 144, respectively).

The introducer core 108 may be utilized in one or more of the passageways in the removal device 100 to assist with positioning thereof. In a preferred configuration, the introducer core 108 is inserted into the first passageway 142 of the vacuum tube 104 to assist in placement thereof. The introducer core 108 preferably extends substantially the entire length of the first passageway to provide a rigid support for the vacuum tube 104 as the vacuum tube 104 is being positioned in the passageway (e.g., urinary tract). The introducer core 108 is preferably detachable such that it may be removed from the second passageway 142 (or other portion of the removal device 100) after placement of the vacuum tube 104 is complete.

The removal device 100 is designed to be optionally utilized with the valve 110 (See FIG. 6) that is in fluid communication with the suction source 148 and is capable of controlling the suction associated with the vacuum tube 104. In one configuration, the valve 110 is a gate valve and may be designed to accommodate tubes and/or portions of the removal device 100 having varying diameters. The valve 110 preferably includes at least two different states, whereby the suction is supplied to the removal device 100 in a first state (i.e., via the vacuum tube 104), and whereby the suction is not supplied to the removal device 100 in a second state. The valve 110 may also include intermediate states that allow the suction to be supplied at a specified level. The valve 110 may further include a safety feature such as an auto-shut down mechanism that terminates the suction once a threshold pressure is breached. Other types of valves may be utilized in conjunction with the removal device as known in the art.

The valve 110 is adapted to be in communication with the suction source 148 via a tube or other mechanism. In one configuration, the suction source 148 is a wall suction as known in the art. In a different configuration, the suction source 148 may be a standard suction unit that is stationary or otherwise portable. In a further configuration, the suction source 148 may be supplied in some other way. In one configuration, a suction source 148 capable of supplying a pressure of about −22 mmHg is utilized, although it should be appreciated that the suction source 148 may supply other pressures as desired.

The removal device 100 may optionally include a sealable port (not shown), for example, such as one that uses a stopcock valve, for infusing or otherwise providing a liquid or other substance into the device 100. In one configuration, saline is infused through one or more of the passageways of the removal device 100 described herein. In this configuration, the suction may be off or paused. In a different configuration, the suction may be used to assist in transporting or otherwise moving the substance through the removal device 100.

Now turning to the use of the removal device 100. In one configuration, the removal device 100 is adapted to be used in a medical setting. In particular, the removal device 100 may be used to remove debris or another foreign object (e.g., kidney stone, diseased tissue, and the like) from a patient (not shown). The debris may reside in one or more organs, orifices, or passageways. Accordingly, the removal device 100 may be utilized in any passageway to assist in removing debris therefrom or adjacent thereto.

In one configuration best seen in FIGS. 7 and 8, the removal device 100 is designed to be positioned in a patient's urinary tract. As depicted in FIG. 7, the sheath 102 is inserted into the patient's urethra (not shown) and extends through the bladder 122 and ureter 112 until being positioned proximate a kidney stone(s) 118, which is most likely disposed in a portion of the urinary tract (e.g., adjacent the kidney 116). The ureteroscope 134 (or other viewing instrument) is inserted into the sheath 102 along with the navigation mechanism 106. The ureteroscope 134 and navigation mechanism 106 are pushed through the sheath 102 until extending through substantially the entirety thereof. The ureteroscope 134 is used to fracture the kidney stone(s) 118 into fragments 180 (see FIG. 8) via a laser or other similar device. After the kidney stone(s) 118 are fractured, the ureteroscope 134 is removed from the sheath 102, and preferably, the navigation mechanism 106 is retained within the sheath 102. Alternatively, in a different configuration, the navigation mechanism 106 may be removed.

As shown in FIG. 8, the vacuum tube 104 is thereafter inserted into the sheath 102 and utilizes the navigation mechanism 106 for guidance thereof. The introducer 108 is disposed within the vacuum tube 104 (e.g., in the first passageway 142) to maintain open communication through the passageways in the vacuum tube 104 during insertion into the patient. Additionally, the second passageway 144 of the vacuum tube 104 is aligned with the navigation mechanism 106. As the vacuum tube 104 is pushed through the sheath 102 (via the introducer 108), the navigation mechanism 106 aligns the second passageway 144 and guides the vacuum tube 104 to the fragments 180. Once the vacuum tube 104 is positioned adjacent the fragments 180, the introducer 108 is detached and removed therefrom. Once the introducer 108 has been removed, the valve 110 is opened to allow access to the suction source 148 and the fragments 180 are pulled from the patient through the removal device 100. A catch or basket (not shown) may be utilized outside of the patient (or in a portion of the removal device 100) to collect the fragments 180, biopsied tissue, and/or other debris.

Figure 9A:
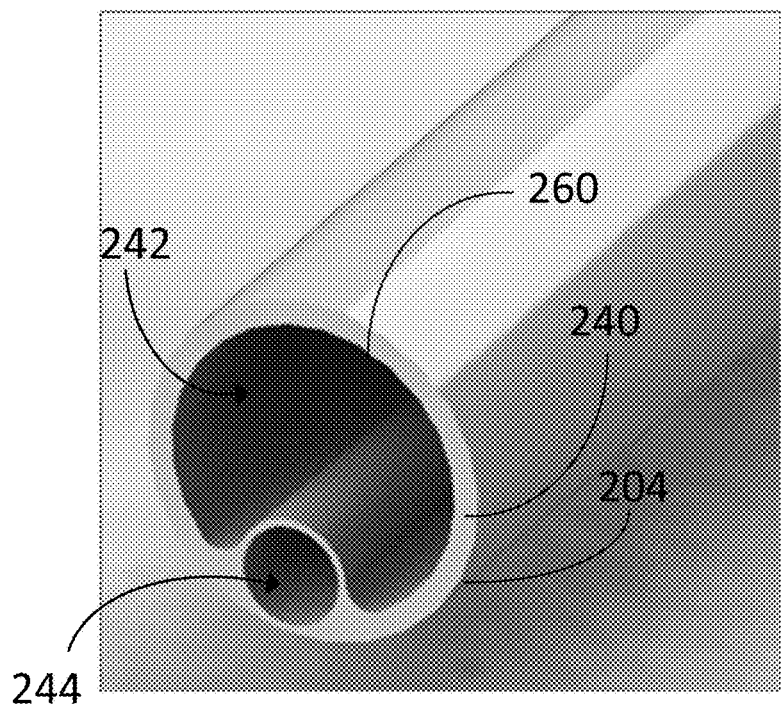
FIG. 9A is a perspective view of a dual lumen vacuum tube that can be used with the removal device of FIG. 1.
Figure 9B:
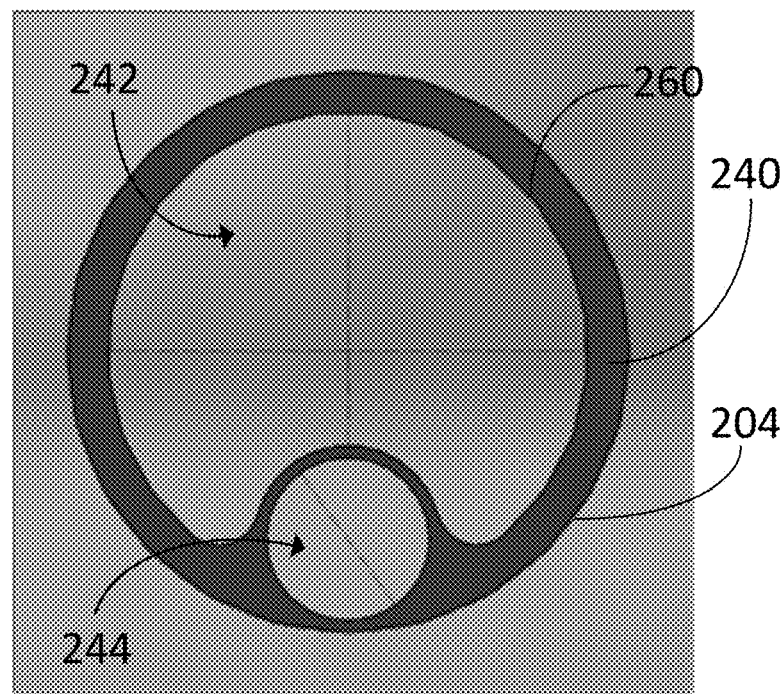
FIG. 9B is a front elevational view of the vacuum tube of FIG. 9A.

Another configuration for a vacuum tube 204 that can be used in connection with removal device 100 is shown in FIGS. 9A and 9B. As shown in FIGS. 9A and 9B, the vacuum tube 204 can be characterized by an elongate dual lumen 240 defined by a first (larger) passageway 242 and a second (smaller) passageway 244 extending longitudinally therethrough. The second passageway 244 can be disposed adjacent an internal surface 260 of the dual lumen 240. For example, as illustrated, the second passageway 244 can share a portion of a wall with the internal surface 260 and/or be fused to the internal surface 260. In one configuration, the first passageway 242 can be used to accommodate suction from the suction source 148 (e.g., as described above in connection with FIG. 6).

Still referencing FIGS. 9A and 9B, the second passageway 244 of the vacuum tube 204 can be configured to accommodate the navigation mechanism 106 (e.g., a guidewire) and/or another device (e.g., ureteroscope 134, another viewing instrument, etc.). Additionally, in some configurations, the first passageway 242 of the vacuum tube 204 can be configured to accommodate the navigation mechanism 106 (e.g., a guidewire) and/or another device (e.g., ureteroscope 134, another viewing instrument, etc.). In some configurations, the second passageway 244 can accommodate the flow of an irrigation fluid from a fluid irrigation source to a distal end of the vacuum tube 204 to facilitate the removal of debris through an in vivo passageway of a patient (e.g., after removal of the navigation mechanism 106 and/or any other device). For example, in one particular non-limiting configuration, the fluid irrigation source can be a syringe connected through any suitable connection, such as a needle that is in fluid communication with the second passageway 244 of the vacuum tube 204, a luer-type connector that is in fluid communication with the second passageway 244 of the vacuum tube 204, and/or any other suitable connector. Pressure can be applied to the syringe to dispense the irrigation fluid through the second passageway 244 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 204 can be configured to selectively provide suction (e.g., through the first passageway 242) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 204.

The first passageway 242 and the second passageway 244 can be configured to be any suitable sizes. For example, in one non-limiting configuration, the first passageway 242 can have internal dimensions of about 3.0 millimeters by 2.09 millimeters, and the second passageway 244 can have a cross-sectional area of about 0.8107 square millimeters.

Figure 10A:
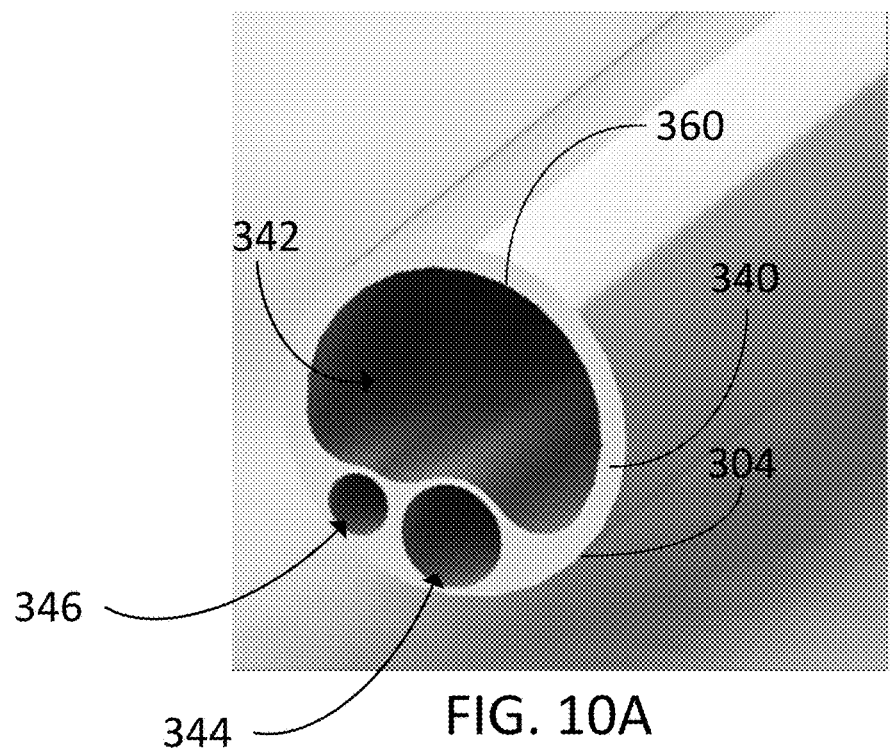
FIG. 10A is a perspective view of a triple lumen vacuum tube that can be used with the removal device of FIG. 1.
Figure 10B:
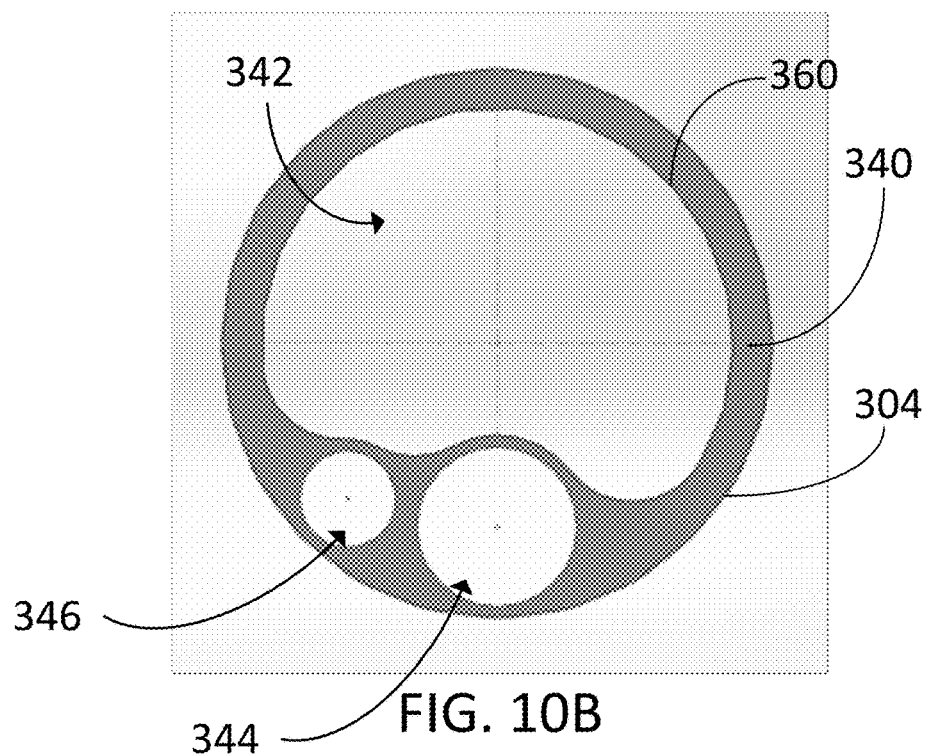
FIG. 10B is a front elevational view of the vacuum tube of FIG. 10A.

FIGS. 10A and 10B show a configuration of a vacuum tube 304 that can be used in connection with the removal device 100. As shown in FIGS. 10A and 10B, the vacuum tube 304 can be characterized by an elongate triple lumen 340 defined by a first passageway 342, a second passageway 344, and a third passageway 346 extending longitudinally therethrough. The second passageway 344 and third passageway 346 can be disposed adjacent an internal surface 360 of the triple lumen 340. For example, as illustrated, the second passageway 344 can share a portion of a wall with the internal surface 360 or be fused to the internal surface 360. As another example, as illustrated, the third passageway 346 can share a portion of a wall with the internal surface 360 and/or second passageway 344. In one configuration, the first passageway 342 can be used to accommodate suction from the suction source 148 (e.g., as described above in connection with FIG. 6).

Still referencing FIGS. 10A and 10B, the second passageway 344 of the vacuum tube 304 can be configured to accommodate the navigation mechanism 106 (e.g., a guidewire) and/or another device (e.g., ureteroscope 134, another viewing instrument, etc.). Additionally, in some configurations, the first passageway 342 of the vacuum tube 304 can be configured to accommodate the navigation mechanism 106 (e.g., a guidewire) and/or another device (e.g., ureteroscope 134, another viewing instrument, etc.). In some configurations, the third passageway 346 can accommodate the flow of an irrigation fluid from a fluid irrigation source to a distal end of the vacuum tube 304 to facilitate the removal of debris from a passageway. For example, in one particular non-limiting configuration, the fluid irrigation source can be a syringe connected through any suitable connection, such as a needle that is in fluid communication with the third passageway 346 of the vacuum tube 304, a luer-type connector that is in fluid communication with the third passageway 346 of the vacuum tube 304, and/or any other suitable connector. Pressure can be applied to the syringe to dispense the irrigation fluid through the third passageway 346 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 304 can be configured to selectively provide suction (e.g., through the first passageway 342) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 304.

The first passageway 342, the second passageway 344, and the third passageway 346 can be configured to be any suitable sizes. For example, in one non-limiting configuration, the first passageway 342 can have internal dimensions of about 3.0 millimeters by 2.09 millimeters, the second passageway 344 can have a cross-sectional area of about 0.8107 square millimeters, and the third passageway can have a cross sectional area of about 0.2919 square millimeters.

Figure 11A:
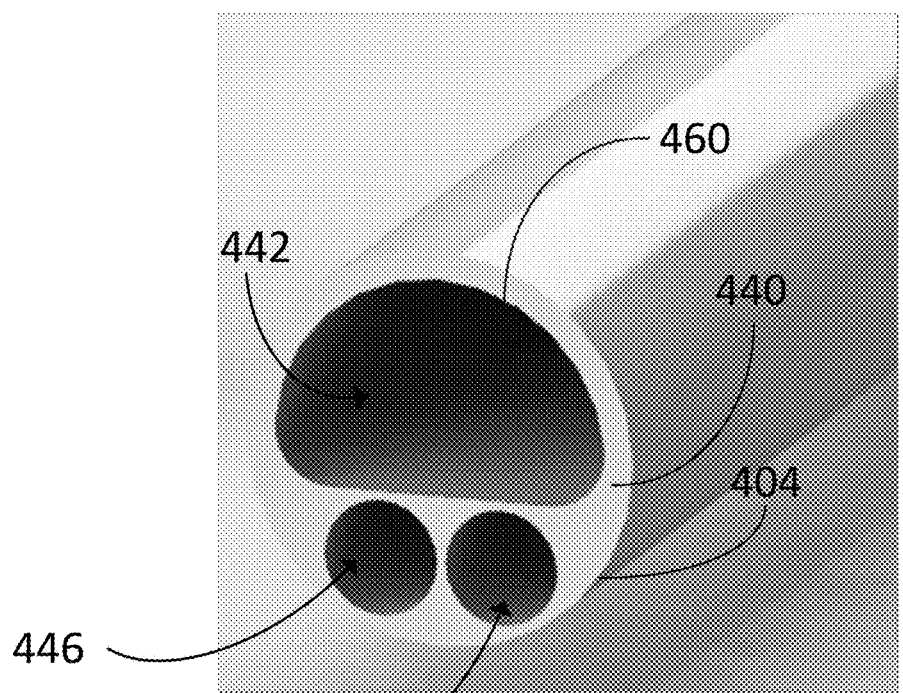
FIG. 11A is a perspective view of another triple lumen vacuum tube that can be used with the removal device of FIG. 1.
Figure 11B:
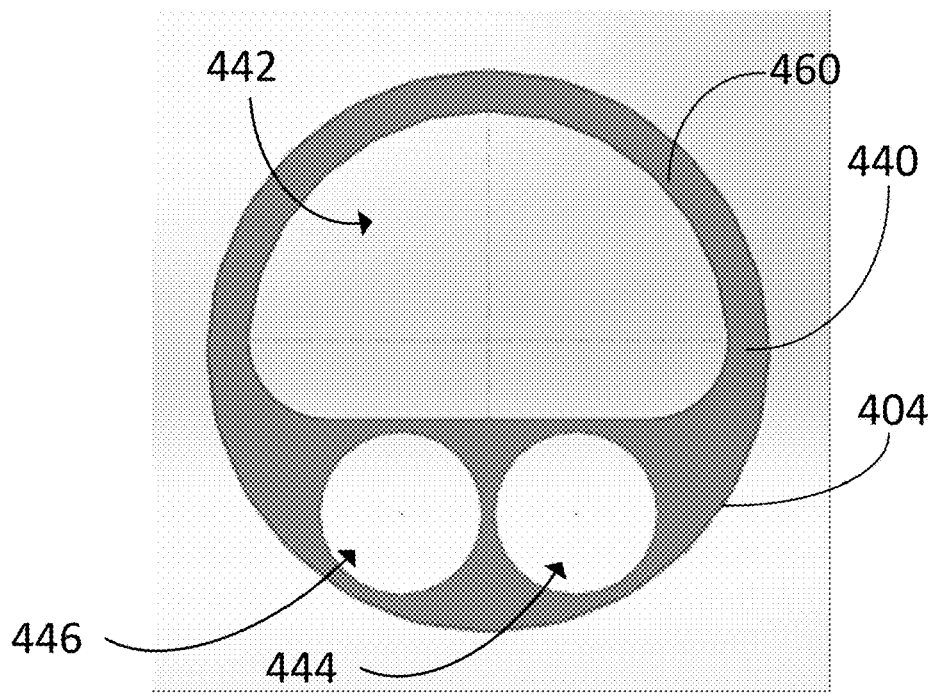
FIG. 11B is a front elevational view of the vacuum tube of FIG. 11A.

FIGS. 11A and 11B show a configuration of a vacuum tube 404 that can be used in connection with the removal device 100. As shown in FIGS. 11A and 11B, the vacuum tube 404 can be characterized by an elongate triple lumen 440 defined by a first passageway 442, a second passageway 444, and a third passageway 446 extending longitudinally therethrough. The second passageway 444 can be disposed adjacent an internal surface 460 of the triple lumen 440. For example, as illustrated, the second passageway 444 can share a portion of a wall with the internal surface 460 or be fused to the internal surface 460. As another example, as illustrated, the third passageway 446 can share a portion of a wall with the internal surface 460 and/or with the second passageway 446, and/or can be fused to the internal surface 460. In one configuration, the first passageway 442 can be used to accommodate suction from the suction source 148 (e.g., as described above in connection with FIG. 6).

Still referencing FIGS. 11A and 11B, the second passageway 444 of the vacuum tube 404 can be configured to accommodate the navigation mechanism 106 (e.g., a guidewire) and/or another device (e.g., ureteroscope 134, another viewing instrument, etc.). Additionally, in some configurations, the first passageway 442 of the vacuum tube 404 can be configured to accommodate the navigation mechanism 106 (e.g., a guidewire) and/or another device (e.g., ureteroscope 134, another viewing instrument, etc.). In some configurations, the third passageway 446 can accommodate the flow of an irrigation fluid from a fluid irrigation source to a distal end of the vacuum tube 404 to facilitate the removal of debris from a passageway. For example, in one particular non-limiting configuration, the fluid irrigation source can be a syringe connected through any suitable connection, such as a needle that is in fluid communication with the third passageway 446 of the vacuum tube 404, a luer-type connector that is in fluid communication with the third passageway 446 of the vacuum tube 404, and/or any other suitable connector. Pressure can be applied to the syringe to dispense the irrigation fluid through the third passageway 446 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art. Additionally or alternatively, the second passageway 444 can accommodate the flow of an irrigation fluid and the third passageway 446 can be configured to accommodate the navigation mechanism 106 (e.g., a guidewire) and/or another device (e.g., ureteroscope 134, another viewing instrument, etc.).

The vacuum tube 404 can be configured to selectively provide suction (e.g., through the first passageway 442) from the suction source (e.g., suction source 148 described above in connection with FIGS. 1-8) before, during and/or after flushing a target region of the in vivo passageway with the irrigation fluid (e.g., via the second passageway 444 and/or the third passageway 446). For example, as described above, the valve 110 (as shown in FIG. 6) can be used to control suction that is supplied to the vacuum tube 404.

The first passageway 442, the second passageway 444, and the third passageway 446 can be configured to be any suitable sizes. For example, in one non-limiting configuration, the first passageway 442 can have internal dimensions of about 3.0 millimeters by 1.93 millimeters, the second passageway 444 can have a cross-sectional area of about 0.8107 square millimeters, and the third passageway 446 can have a cross sectional area of about 0.8107 square millimeters.

Figure 12A:
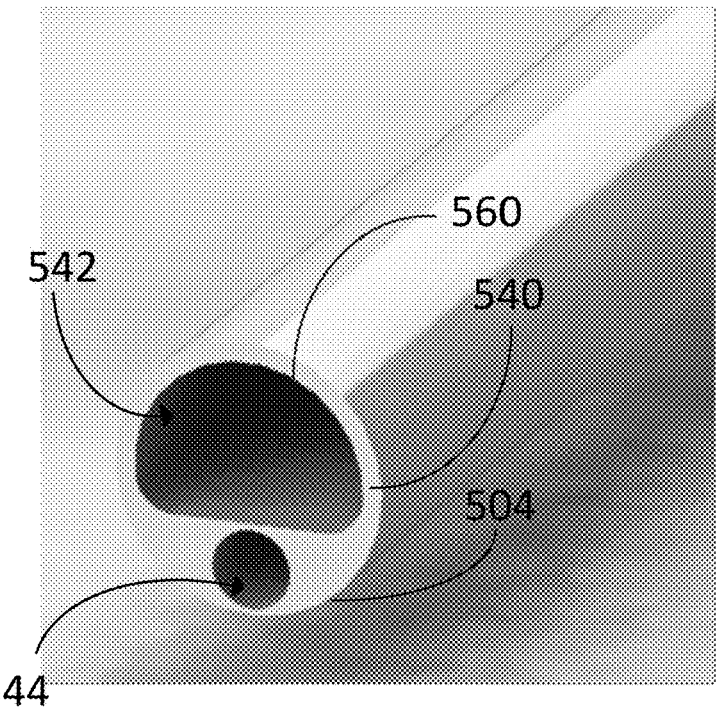
FIG. 12A is a perspective view of another dual lumen vacuum tube that can be used with the removal device of FIG. 1.
Figure 12B:
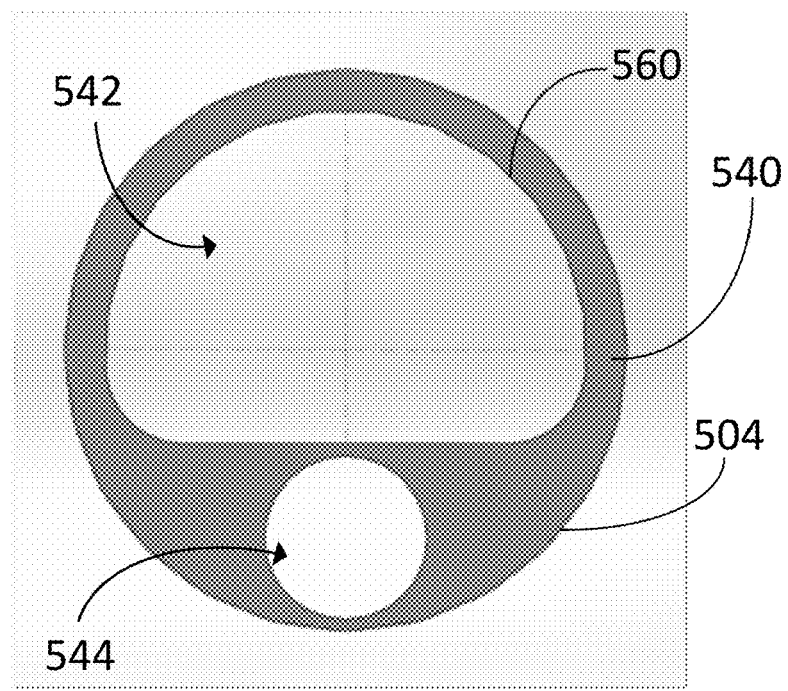
FIG. 12B is a front elevational view of the vacuum tube of FIG. 12A.

FIGS. 12A and 12B show a configuration of a vacuum tube 504 that can be used in connection with the removal device 100. As shown in FIGS. 12A and 12B, the vacuum tube 504 can be characterized by an elongate dual lumen 540 defined by a first (larger) passageway 542 and a second (smaller) passageway 544 extending longitudinally therethrough. The second passageway 544 can be disposed adjacent an internal surface 560 of the dual lumen 540. For example, as illustrated, the second passageway 544 can share a portion of a wall with the internal surface 560 and/or can be fused to the internal surface 560. In one configuration, the first passageway 542 can be used to accommodate suction from the suction source 148 (e.g., as described above in connection with FIG. 6).

Still referencing FIGS. 12A and 12B, the second passageway 544 of the vacuum tube 504 can be configured to accommodate the navigation mechanism 106 (e.g., a guidewire) and/or another device (e.g., ureteroscope 134, another viewing instrument, etc.). Additionally, in some configurations, the first passageway 542 of the vacuum tube 504 can be configured to accommodate the navigation mechanism 106 (e.g., a guidewire) and/or another device (e.g., ureteroscope 134, another viewing instrument, etc.). In some configurations, the second passageway 544 can accommodate the flow of an irrigation fluid from a fluid irrigation source to a distal end of the vacuum tube 504 to facilitate the removal of debris through an in vivo passageway of a patient (e.g., after removal of the navigation mechanism 106 and/or any other device). For example, in one particular non-limiting configuration, the fluid irrigation source can be a syringe connected through any suitable connection, such as a needle that is in fluid communication with the second passageway 544 of the vacuum tube 504, a luer-type connector that is in fluid communication with the second passageway 544 of the vacuum tube 504, and/or any other suitable connector. Pressure can be applied to the syringe to dispense the irrigation fluid through the second passageway 544 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 504 can be configured to selectively provide suction (e.g., through the first passageway 542) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 504.

The first passageway 542 and the second passageway 544 can be configured to be any suitable sizes. For example, in one non-limiting configuration, the first passageway 542 can have internal dimensions of about 3.0 millimeters by 2.09 millimeters, and the second passageway 544 can have a cross-sectional area of about 0.8107 square millimeters.

Figure 13A:
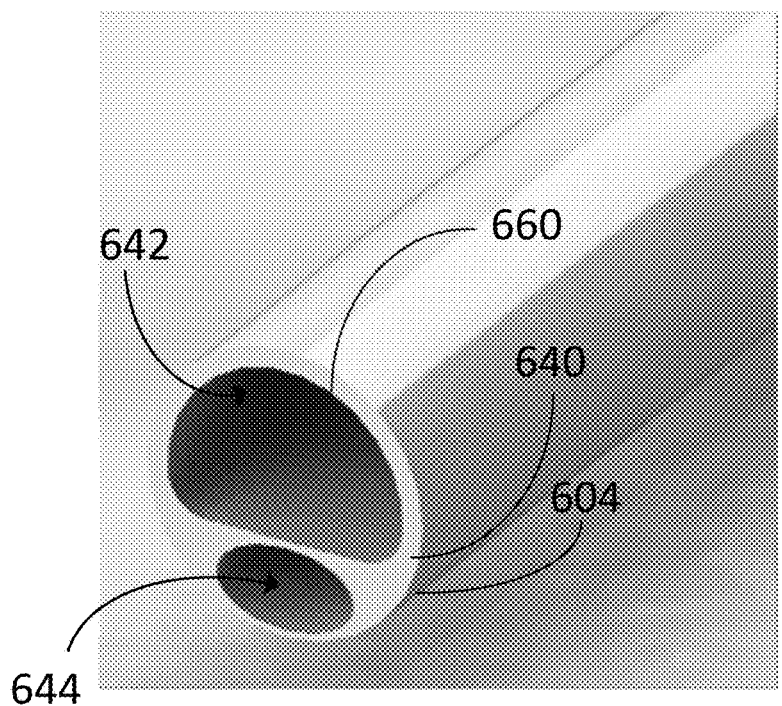
FIG. 13A is a perspective view of yet another dual lumen vacuum tube that can be used with the removal device of FIG. 1.
Figure 13B:
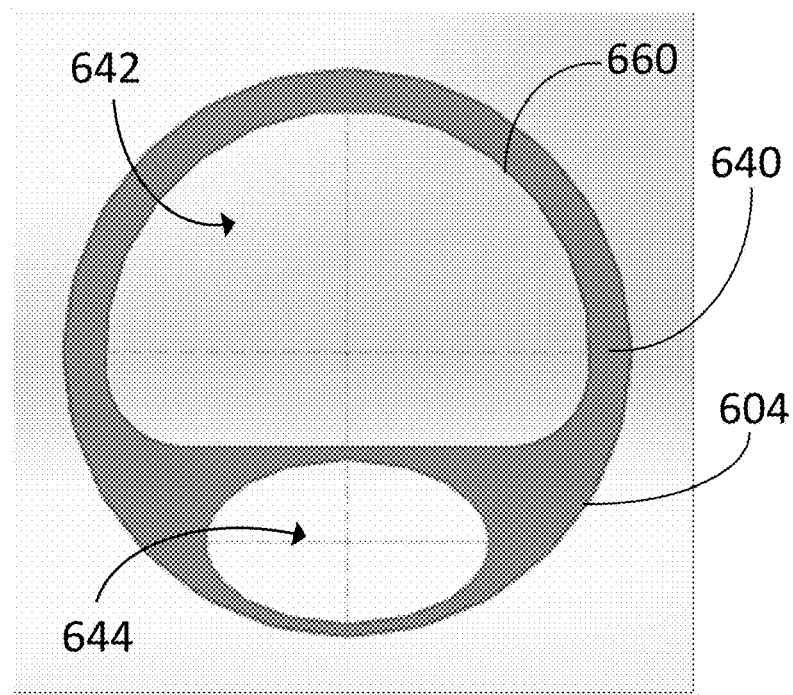
FIG. 13B is a front elevational view of the vacuum tube of FIG. 13A.

FIGS. 13A and 13B show a configuration of a vacuum tube 604 that can be used in connection with the removal device 100. As shown in FIGS. 13A and 13B, the vacuum tube 604 can be characterized by an elongate dual lumen 640 defined by a first (larger) passageway 642 and a second (smaller) passageway 644 extending longitudinally therethrough. As illustrated, the second passageway 644 of vacuum tube 604 can have an elongate cross section. The second passageway 644 can be disposed adjacent an internal surface 660 of the dual lumen 640. For example, as illustrated, the second passageway 644 can share a portion of a wall with the internal surface 660 and/or can be fused to the internal surface 660. In one configuration, the first passageway 642 can be used to accommodate suction from the suction source 148 (e.g., as described above in connection with FIG. 6).

Still referencing FIGS. 13A and 13B, the second passageway 644 of the vacuum tube 604 can be configured to accommodate the navigation mechanism 106 (e.g., a guidewire) and/or another device (e.g., ureteroscope 134, another viewing instrument, etc.). Additionally, in some configurations, the first passageway 642 of the vacuum tube 604 can be configured to accommodate the navigation mechanism 106 (e.g., a guidewire) and/or another device (e.g., ureteroscope 134, another viewing instrument, etc.). In some configurations, the second passageway 644 can simultaneously accommodate the flow of an irrigation fluid from a fluid irrigation source to a distal end of the vacuum tube 604 to facilitate the removal of debris through an in vivo passageway of a patient. For example, in one particular non-limiting configuration, the fluid irrigation source can be a syringe connected through any suitable connection, such as a needle that is in fluid communication with the second passageway 644 of the vacuum tube 604, a luer-type connector that is in fluid communication with the second passageway 644 of the vacuum tube 604, and/or any other suitable connector. Pressure can be applied to the syringe to dispense the irrigation fluid through the second passageway 644 in the direction of the object to be removed. In such an example, the irrigation fluid can flow through the second passageway 644 while the navigation mechanism (and/or any other suitable device) is in place in the second passageway 644. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 604 can be configured to selectively provide suction (e.g., through the first passageway 642) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 604.

The first passageway 642 and the second passageway 644 can be configured to be any suitable sizes. For example, in one non-limiting configuration, the first passageway 642 can have internal dimensions of about 3.0 millimeters by 2.09 millimeters, and the second passageway 644 can have a cross-sectional area of about 1.4757 square millimeters, which can provide a cross-sectional area of about 0.665 square millimeters available for irrigation fluid to pass while a guidewire (and/or other suitable device) having a cross-sectional area of about 0.8107 square millimeters is in place.

Figure 14A:
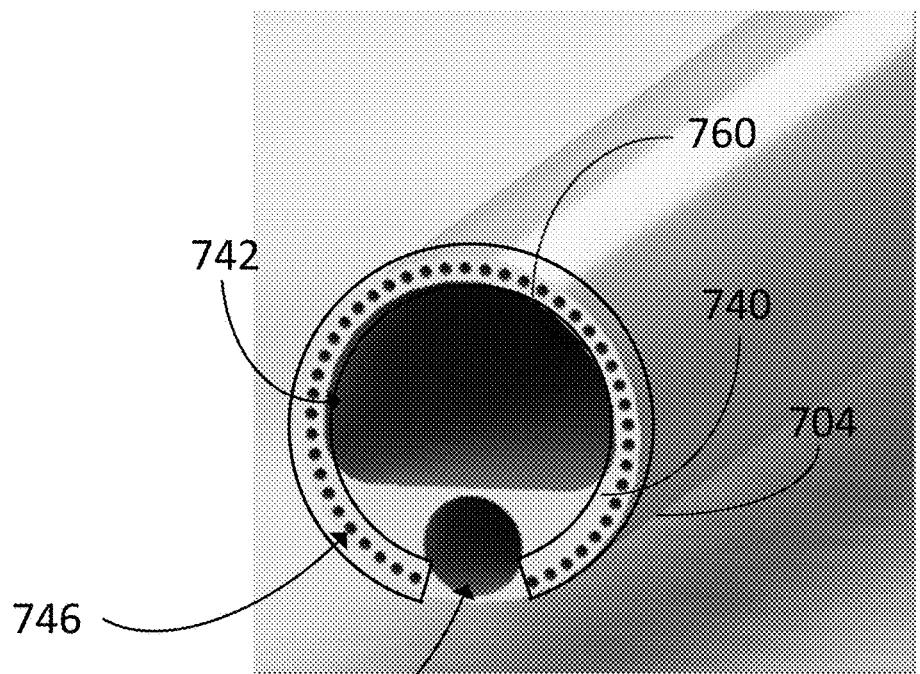
FIG. 14A is a perspective view of a vacuum tube with peripheral passageways that can be used with the removal device of FIG. 1.
Figure 14B:
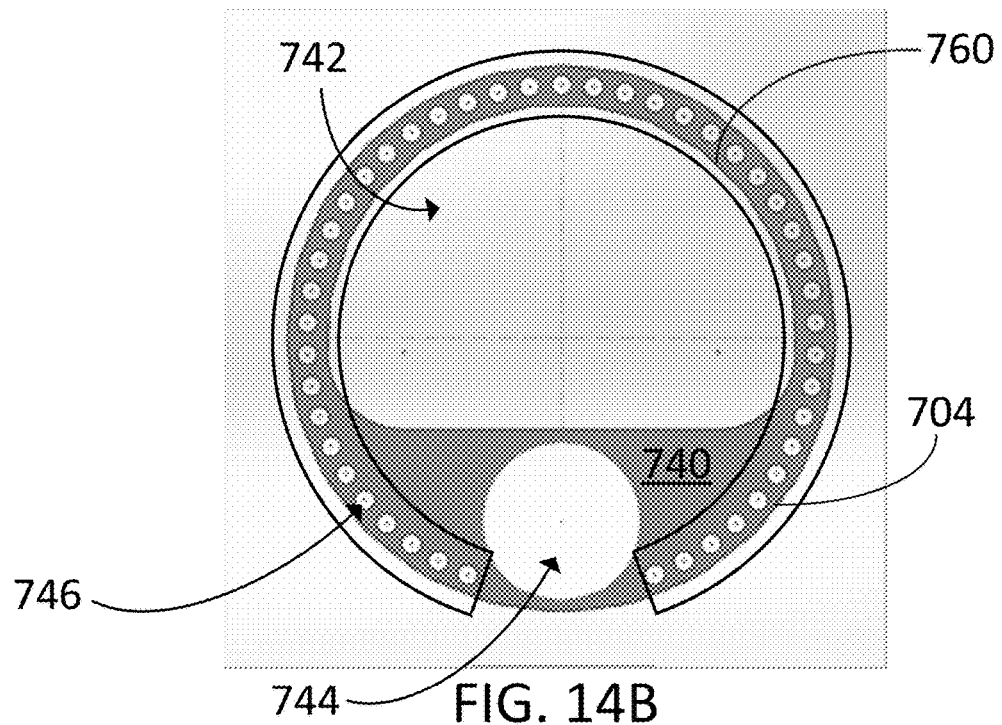
FIG. 14B is a front elevational view of the vacuum tube of FIG. 14A.

FIGS. 14A and 14B show a configuration of a vacuum tube 704 that can be used in connection with the removal device 100. As shown in FIGS. 14A and 14B, the vacuum tube 704 can be characterized by a lumen 740 defined by a first passageway 742, a second passageway 744, and many peripheral passageways 746 extending longitudinally therethrough. The second passageway 744 can be disposed adjacent an internal surface 760 of the lumen 740. For example, as illustrated, the second passageway 744 can share a portion of a wall with the internal surface 760 and/or can be fused to the internal surface 760. As another example, as illustrated, the peripheral passageways 746 can each be disposed within a portion of the wall of vacuum tube 704 between the internal surface 760 and an external surface of the vacuum tube 704. In one configuration, the first passageway 742 can be used to accommodate suction from the suction source 148 (e.g., as described above in connection with FIG. 6).

Still referencing FIGS. 14A and 14B, the second passageway 744 of the vacuum tube 704 can be configured to accommodate the navigation mechanism 106 (e.g., a guidewire) and/or another device (e.g., ureteroscope 134, another viewing instrument, etc.). Additionally, in some configurations, the first passageway 742 of the vacuum tube 704 can be configured to accommodate the navigation mechanism 106 (e.g., a guidewire) and/or another device (e.g., ureteroscope 134, another viewing instrument, etc.). In some configurations, the peripheral passageways 746 can collectively accommodate the flow of an irrigation fluid from a fluid irrigation source to a distal end of the vacuum tube 704 to facilitate the removal of debris through an in vivo passageway of a patient. For example, in one particular non-limiting configuration, the fluid irrigation source can be a syringe connected through any suitable connection, such as a needle that is in fluid communication with the peripheral passageways 746 of the vacuum tube 704, a luer-type connector that is in fluid communication with the peripheral passageways 746 of the vacuum tube 704, and/or any other suitable connector. Pressure can be applied to the syringe to dispense the irrigation fluid through the peripheral passageways 746 in the direction of the object to be removed. In other non-limiting examples, in addition to, and/or in lieu of, the syringe described above, the fluid irrigation source can include a wash bottle, a positive displacement pump, and/or any other suitable fluid irrigation sources known to those skilled in the art.

The vacuum tube 704 can be configured to selectively provide suction (e.g., through the first passageway 742) from the suction source (e.g., suction source 148 described above in connection with FIGS. 1-8) before, during and/or after flushing a target region of the in vivo passageway with the irrigation fluid (e.g., via the second passageway 744 and/or the peripheral passageways 746). For example, as described above, the valve 110 (as shown in FIG. 6) can be used to control suction that is supplied to the vacuum tube 704.

The first passageway 742, the second passageway 744, and the peripheral passageways 746 can be configured to be any suitable sizes. For example, in one non-limiting configuration, the first passageway 742 can have internal dimensions of about 3.0 millimeters by 2.09 millimeters, the second passageway 744 can have a cross-sectional area of about 0.8107 square millimeters, and the peripheral passageways 746 can have a combined cross-sectional area of about 0.635 square millimeters.

Figure 15A:
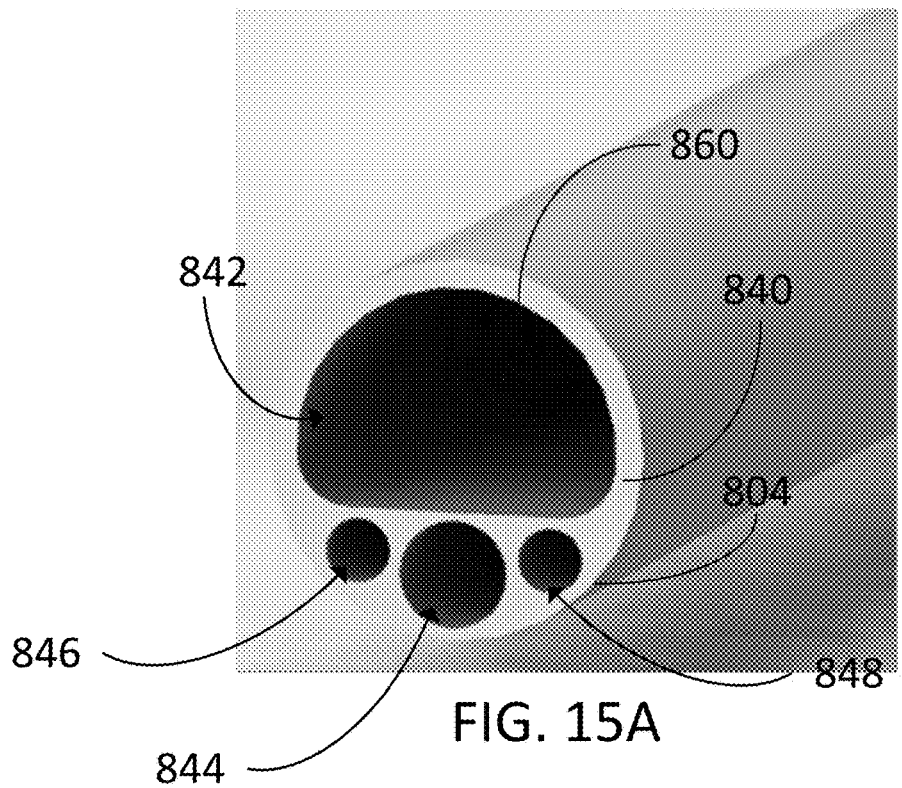
FIG. 15A is a perspective view of a quadruple lumen vacuum tube that can be used with the removal device of FIG. 1.
Figure 15B:
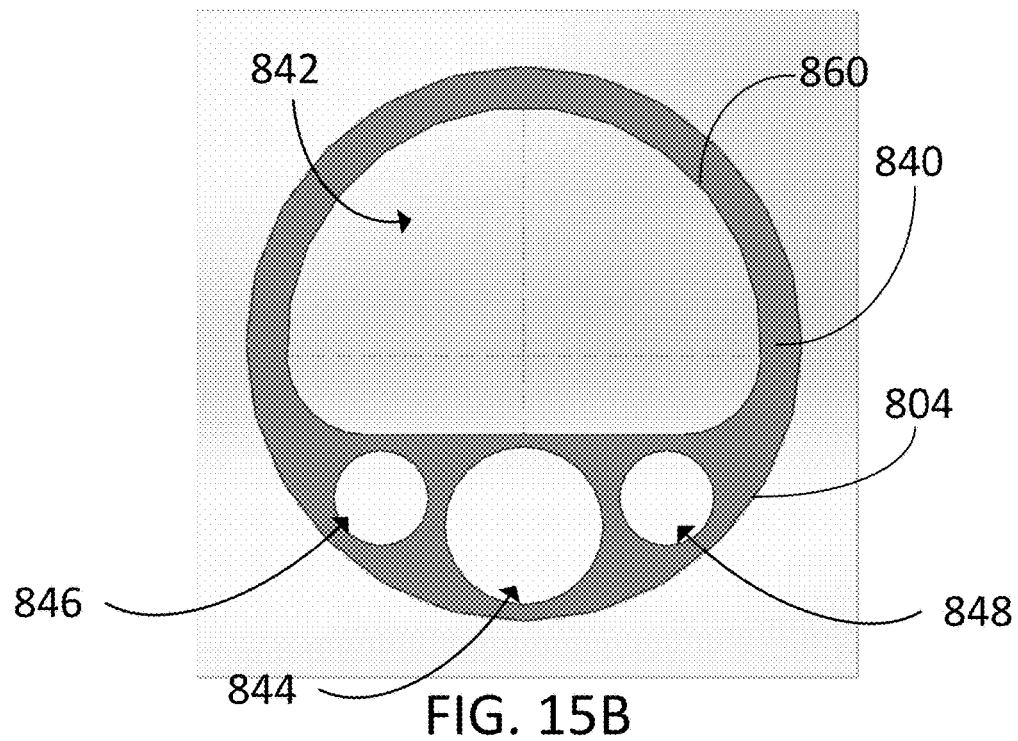
FIG. 15B is a front elevational view of the vacuum tube of FIG. 15A.

FIGS. 15A and 15B show a configuration of a vacuum tube 804 that can be used in connection with the removal device 100. As shown in FIGS. 15A and 15B, the vacuum tube 804 can be characterized by an elongate quadruple lumen 840 defined by a first passageway 842, a second passageway 844, a third passageway 846, and a fourth passageway 848 extending longitudinally therethrough. Each of the second passageway 844, the third passageway 846 and the fourth passageway 848 can be disposed adjacent an internal surface 860 of the quadruple lumen 840. For example, as illustrated, the second passageway 844 can share a portion of a wall with the internal surface 860 and/or can be fused to the internal surface 860. As another example, as illustrated, the third passageway 846 can share a portion of a wall with the internal surface 860 and/or with the second passageway 846, and/or can be fused to the internal surface 860. In one configuration, the first passageway 842 can be used to accommodate suction from the suction source 148 (e.g., as described above in connection with FIG. 6).

Still referencing FIGS. 15A and 15B, the second passageway 844 of the vacuum tube 804 can be configured to accommodate the navigation mechanism 106 (e.g., a guidewire) and/or another device (e.g., ureteroscope 134, another viewing instrument, etc.). Additionally, in some configurations, the first passageway 842 of the vacuum tube 804 can be configured to accommodate the navigation mechanism 106 (e.g., a guidewire) and/or another device (e.g., ureteroscope 134, another viewing instrument, etc.). In some configurations, the third passageway 846 can accommodate the flow of an irrigation fluid from a fluid irrigation source to a distal end of the vacuum tube 804 to facilitate the removal of debris from a passageway. For example, in one particular non-limiting configuration, the fluid irrigation source can be a syringe connected through any suitable connection, such as a needle that is in fluid communication with the third passageway 846 and/or the fourth passageway 848 of the vacuum tube 804, a luer-type connector that is in fluid communication with the third passageway 846 and/or the fourth passageway 848 of the vacuum tube 804, and/or any other suitable connector. Pressure can be applied to the syringe to dispense the irrigation fluid through the third passageway 846 and/or the fourth passageway 848 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 804 can be configured to selectively provide suction (e.g., through the first passageway 842) from the suction source (e.g., suction source 148 described above in connection with FIGS. 1-8) before, during and/or after flushing a target region of the in vivo passageway with the irrigation fluid (e.g., via the third passageway 446 and/or the fourth passageway 448). For example, as described above, the valve 110 (as shown in FIG. 6) can be used to control suction that is supplied to the vacuum tube 804.

The first passageway 842, the second passageway 844, the third passageway 846, and the fourth passageway 848 can be configured to be any suitable sizes. For example, in one non-limiting configuration, the first passageway 842 can have internal dimensions of about 2.99 millimeters by 2.07 millimeters, the second passageway 844 can have a cross-sectional area of about 0.8107 square millimeters, and the third passageway 846 and the fourth passageway 848 can have a combined cross-sectional area of about 0.5654 square millimeters.

Figure 16A:
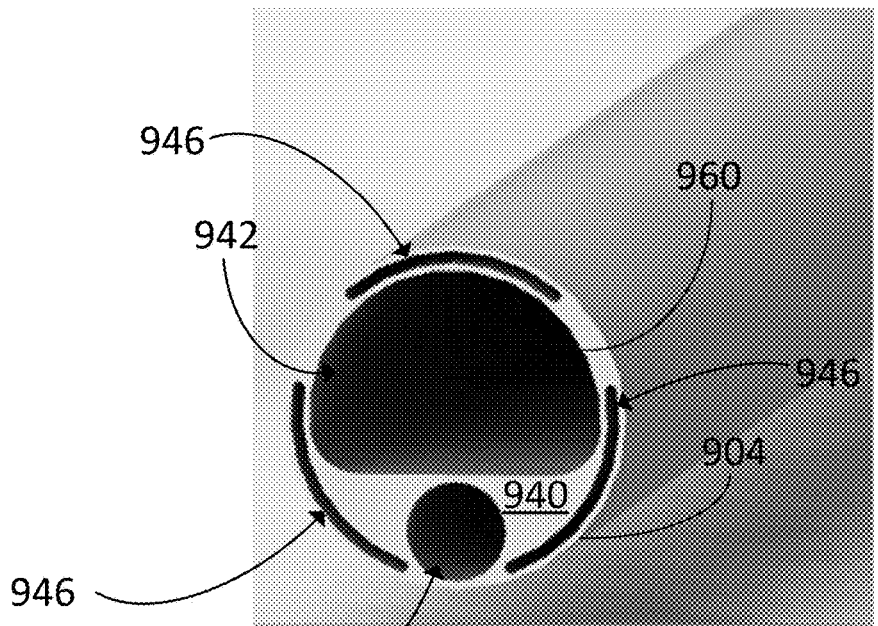
FIG. 16A is a perspective view of another vacuum tube with peripheral passageways that can be used with the removal device of FIG. 1.
Figure 16B:
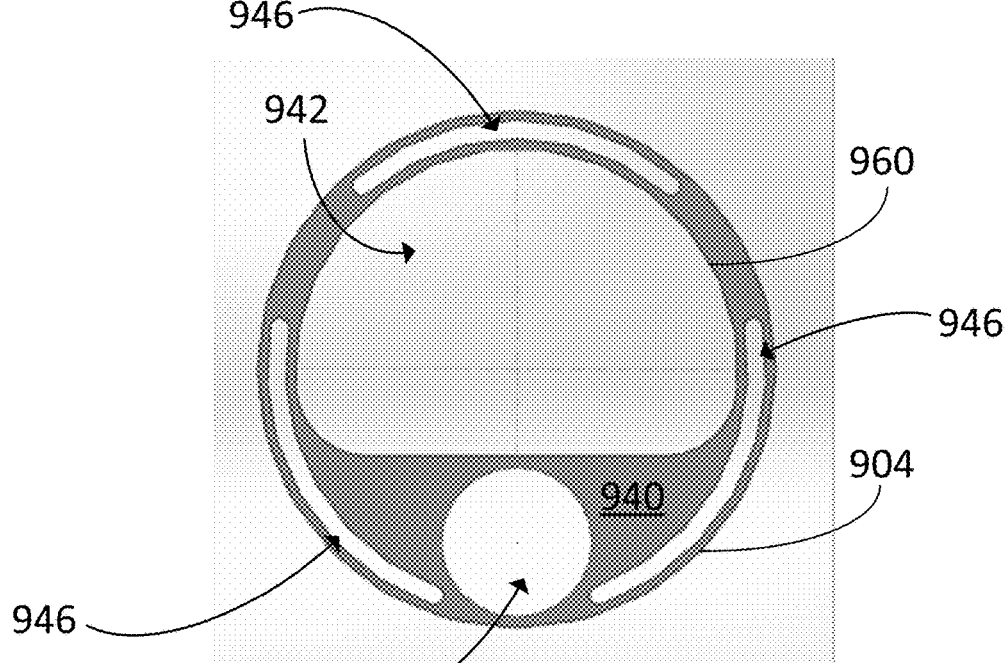
FIG. 16B is a front elevational view of the vacuum tube of FIG. 16A.

FIGS. 16A and 16B show a configuration of a vacuum tube 904 that can be used in connection with the removal device 100. As shown in FIGS. 16A and 16B, the vacuum tube 904 can be characterized by a lumen 940 defined by a first passageway 942, a second passageway 944, and three peripheral passageways 946 extending longitudinally therethrough. The second passageway 944 can be disposed adjacent an internal surface 960 of the lumen 940. For example, as illustrated, the second passageway 944 can share a portion of a wall with the internal surface 960 and/or can be fused to the internal surface 960. As another example, as illustrated, the peripheral passageways 946 can each be disposed within a portion of the wall of vacuum tube 904 between the internal surface 960 and an external surface of the vacuum tube 904. In one configuration, the first passageway 942 can be used to accommodate suction from the suction source 148 (e.g., as described above in connection with FIG. 6).

Still referencing FIGS. 16A and 16B, the second passageway 944 of the vacuum tube 904 can be configured to accommodate the navigation mechanism 106 (e.g., a guidewire) and/or another device (e.g., ureteroscope 134, another viewing instrument, etc.). Additionally, in some configurations, the first passageway 942 of the vacuum tube 904 can be configured to accommodate the navigation mechanism 106 (e.g., a guidewire) and/or another device (e.g., ureteroscope 134, another viewing instrument, etc.). In some configurations, the peripheral passageways 946 can collectively accommodate the flow of an irrigation fluid from a fluid irrigation source to a distal end of the vacuum tube 904 to facilitate the removal of debris through an in vivo passageway of a patient. For example, in one particular non-limiting configuration, the fluid irrigation source can be a syringe connected through any suitable connection, such as a needle that is in fluid communication with the peripheral passageways 946 of the vacuum tube 904, a luer-type connector that is in fluid communication with the peripheral passageways 946 of the vacuum tube 904, and/or any other suitable connector. Pressure can be applied to the syringe to dispense the irrigation fluid through the peripheral passageways 946 in the direction of the object to be removed. In other non-limiting examples, in addition to, and/or in lieu of, the syringe described above, the fluid irrigation source can include a wash bottle, a positive displacement pump, and/or any other suitable fluid irrigation sources known to those skilled in the art.

The vacuum tube 904 can be configured to selectively provide suction (e.g., through the first passageway 942) from the suction source (e.g., suction source 148 described above in connection with FIGS. 1-8) before, during and/or after flushing a target region of the in vivo passageway with the irrigation fluid (e.g., via the second passageway 944 and/or the peripheral passageways 946). For example, as described above, the valve 110 (as shown in FIG. 6) can be used to control suction that is supplied to the vacuum tube 904.

The first passageway 942, the second passageway 944, and the peripheral passageways 946 can be configured to be any suitable sizes. For example, in one non-limiting configuration, the first passageway 942 can have internal dimensions of about 3.0 millimeters by 2.09 millimeters, the second passageway 944 can have a cross-sectional area of about 0.8107 square millimeters, and the peripheral passageways 946 can have a combined cross-sectional area of about 0.9036 square millimeters.

Figure 17A:
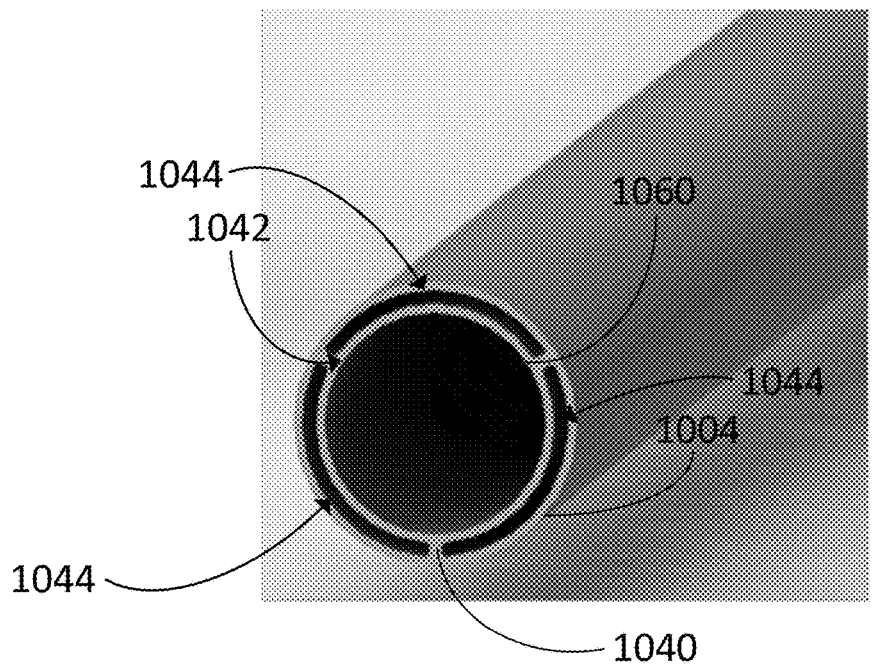
FIG. 17A is a perspective view of yet another vacuum tube with peripheral passageways that can be used with the removal device of FIG. 1.
Figure 17B:
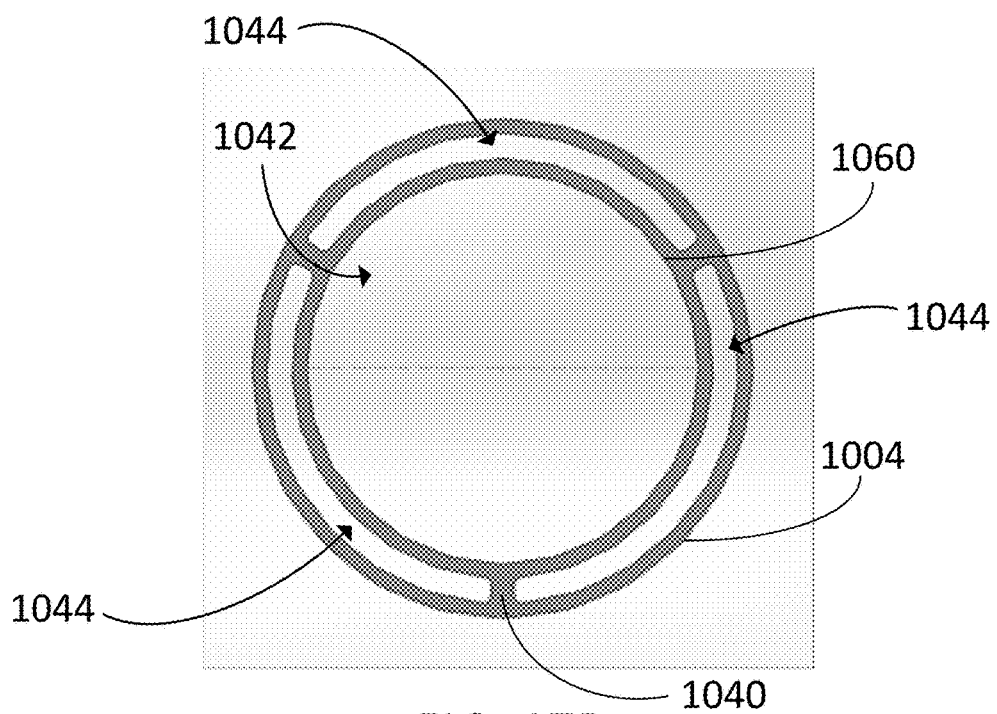
FIG. 17B is a front elevational view of the vacuum tube of FIG. 17A.

FIGS. 17A and 17B show a configuration of a vacuum tube 1004 that can be used in connection with the removal device 100. As shown in FIGS. 17A and 17B, the vacuum tube 1004 can be characterized by a lumen 1040 defined by a first passageway 1042, and three peripheral passageways 1044 extending longitudinally therethrough. The peripheral passageways 1044 can each be disposed within a portion of the wall of vacuum tube 1004 between the internal surface 1060 and an external surface of the vacuum tube 1004. In one configuration, the first passageway 1042 can be used to accommodate suction from the suction source 148 (e.g., as described above in connection with FIG. 6).

Still referencing FIGS. 17A and 17B, the first passageway of the vacuum tube 1004 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the peripheral passageways 1044 can collectively accommodate the flow of an irrigation fluid from a fluid irrigation source to a distal end of the vacuum tube 1004 to facilitate the removal of debris through an in vivo passageway of a patient. For example, in one particular non-limiting configuration, the fluid irrigation source can be a syringe connected through any suitable connection, such as a needle that is in fluid communication with the peripheral passageways 1044 of the vacuum tube 1004, a luer-type connector that is in fluid communication with the peripheral passageways 1044 of the vacuum tube 1004, and/or any other suitable connector. Pressure can be applied to the syringe to dispense the irrigation fluid through the peripheral passageways 1044 in the direction of the object to be removed. In other non-limiting examples, in addition to, and/or in lieu of, the syringe described above, the fluid irrigation source can include a wash bottle, a positive displacement pump, and/or any other suitable fluid irrigation sources known to those skilled in the art.

The vacuum tube 1004 can be configured to selectively provide suction (e.g., through the first passageway 1042) from the suction source (e.g., suction source 148 described above in connection with FIGS. 1-8) before, during and/or after flushing a target region of the in vivo passageway with the irrigation fluid (e.g., via the peripheral passageways 1044). For example, as described above, the valve 110 (as shown in FIG. 6) can be used to control suction that is supplied to the vacuum tube 1004.

The first passageway 1042 and the peripheral passageways 1044 can be configured to be any suitable sizes. For example, in one non-limiting configuration, the first passageway 1042 can have an internal diameter of about 2.75 millimeters, and the peripheral passageways 1044 can have a combined cross-sectional area of about 1.6527 square millimeters.

Figure 18A:
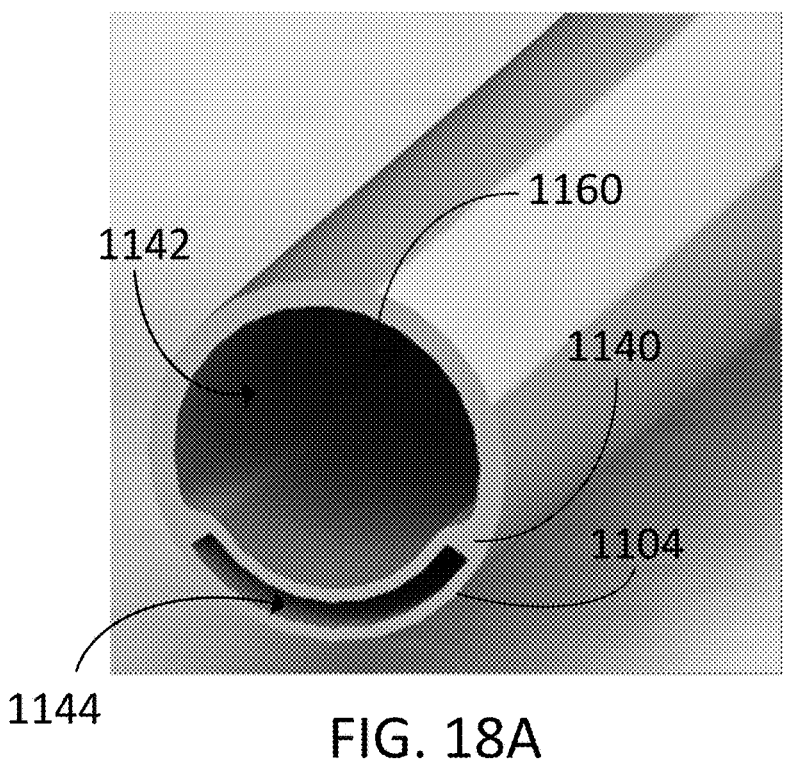
FIG. 18A is a perspective view of still another dual lumen vacuum tube with peripheral passageways that can be used with the removal device of FIG. 1.
Figure 18B:
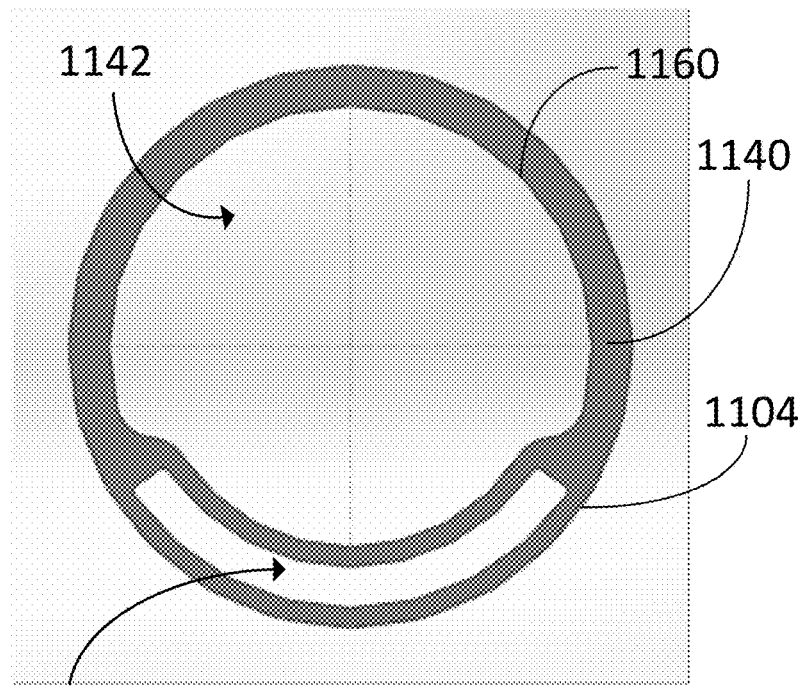
FIG. 18B is a front elevational view of the vacuum tube of FIG. 18A.

FIGS. 18A and 18B show a configuration of a vacuum tube 1104 that can be used in connection with the removal device 100. As shown in FIGS. 18A and 18B, the vacuum tube 1104 can be characterized by an elongate dual lumen 1140 defined by a first passageway 1142 and a second passageway 1144 extending longitudinally therethrough. The second passageway 1144 can be disposed adjacent an internal surface 1160 of the dual lumen 1140. For example, as illustrated, the second passageway 1144 can form at least a portion of the internal surface 1160 and/or can be fused to the internal surface 1160. In one configuration, the first passageway 1142 can be used to accommodate suction from the suction source 148 (e.g., as described above in connection with FIG. 6).

Still referencing FIGS. 18A and 18B, the first passageway 1142 of the vacuum tube 1104 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the second passageway 1144 can accommodate the flow of an irrigation fluid from a fluid irrigation source to a distal end of the vacuum tube 1104 to facilitate the removal of debris through an in vivo passageway of a patient. For example, in one particular non-limiting configuration, the fluid irrigation source can be a syringe connected through any suitable connection, such as a needle that is in fluid communication with the second passageway 1144 of the vacuum tube 1104, a luer-type connector that is in fluid communication with the second passageway 1144 of the vacuum tube 1104, and/or any other suitable connector. Pressure can be applied to the syringe to dispense the irrigation fluid through the second passageway 1144 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 1104 can be configured to selectively provide suction (e.g., through the first passageway 1142) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1104.

The first passageway 1142 and the second passageway 1144 can be configured to be any suitable sizes. For example, in one non-limiting configuration, the first passageway 1142 can have internal dimensions of about 3.0 millimeters by 2.75 millimeters, and the second passageway 1144 can have a cross-sectional area of about 0.7566 square millimeters.

Figure 19A:
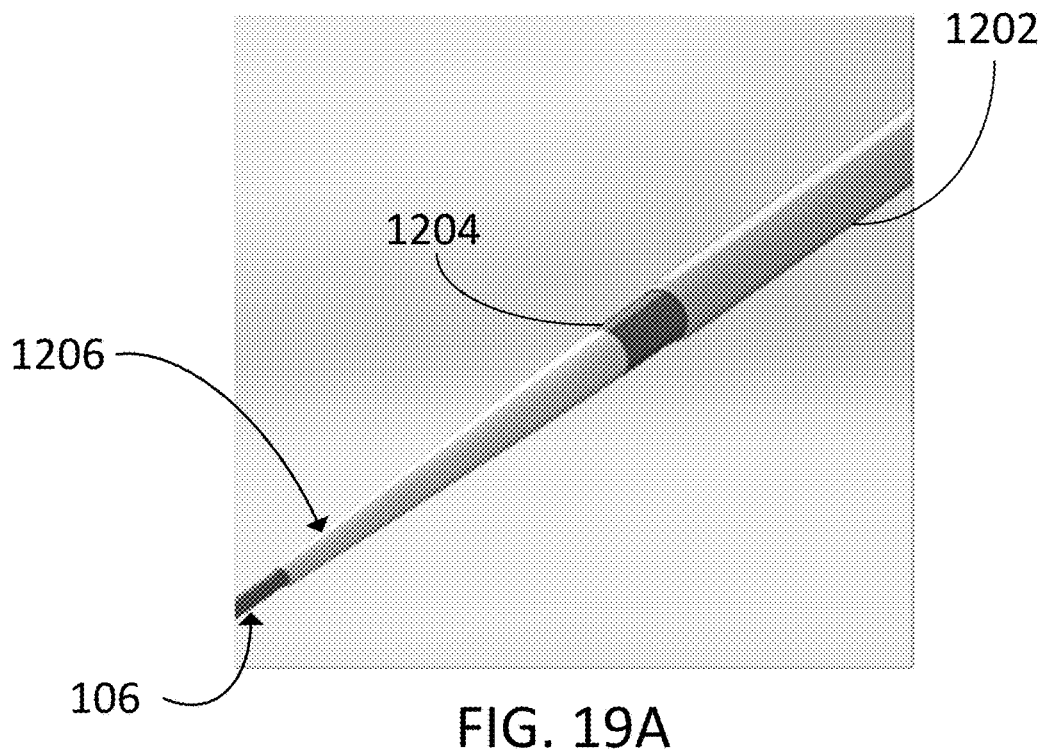
FIG. 19A is a perspective view of another vacuum tube that can be used with the removal device of FIG. 1.
Figure 19B:
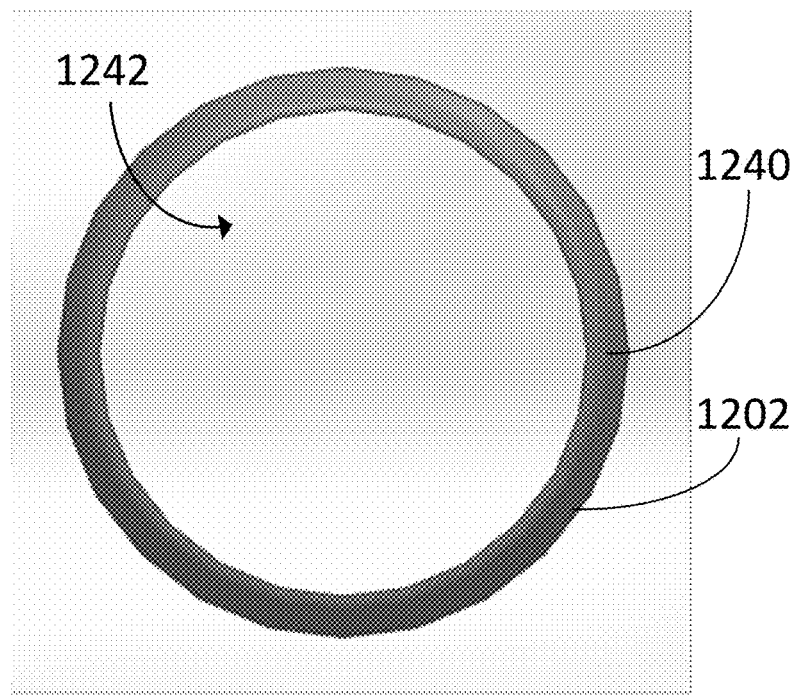
FIG. 19B is a front elevational view of the vacuum tube of FIG. 19A.

FIGS. 19A and 19B show a configuration of a vacuum tube 1202 that can be used in connection with the removal device 100. As shown in FIGS. 19A and 19B, the vacuum tube 1202 can be characterized by an elongate lumen 1240 defined by a passageway 1242. As illustrated, vacuum tube 1202 can be introduced into the ureter 112 and/or kidney 116 using an obturator 1204 having a tip 1206.

Still referencing FIGS. 19A and 19B, the passageway 1242 of the vacuum tube 1202 can be configured to accommodate the obturator 1204 and/or the navigation mechanism 106 (e.g., a guidewire) and/or another device (e.g., ureteroscope 134, another viewing instrument, etc.). In such a configuration, the navigation mechanism 106, obturator 1204, and/or another device can be removed from the passageway 1242 prior to providing suction or, in some embodiments, left in place while suction is provided. In some configurations, the passageway 1242 can accommodate the flow of an irrigation fluid from a fluid irrigation source to a distal end of the vacuum tube 1202 to facilitate the removal of debris through an in vivo passageway of a patient (e.g., after removal of the navigation mechanism 106, obturator 1204, and/or any other device). For example, in one particular non-limiting configuration, the fluid irrigation source can be a syringe connected through any suitable connection, such as a needle that is in fluid communication with the passageway 1242 of the vacuum tube 1202, a luer-type connector that is in fluid communication with the passageway 1242 of the vacuum tube 1202, and/or any other suitable connector. Pressure can be applied to the syringe to dispense the irrigation fluid through the second passageway 1242 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 1202 can be configured to selectively provide suction (e.g., through the first passageway 1242) from the suction source (e.g., suction source 148 described above in connection with FIGS. 1-8) before and/or after flushing a target region of the in vivo passageway with the irrigation fluid though the passageway 1242. For example, as described above, the valve 110 (as shown in FIG. 6) can be used to control suction that is supplied to the vacuum tube 1202.

The passageway 1242 can be configured to be any suitable sizes. For example, in one non-limiting configuration, the passageway 1242 can have an internal diameter of about 3.0 millimeters, and a cross-sectional area of about 7.0686 square millimeters.

Figure 20A:
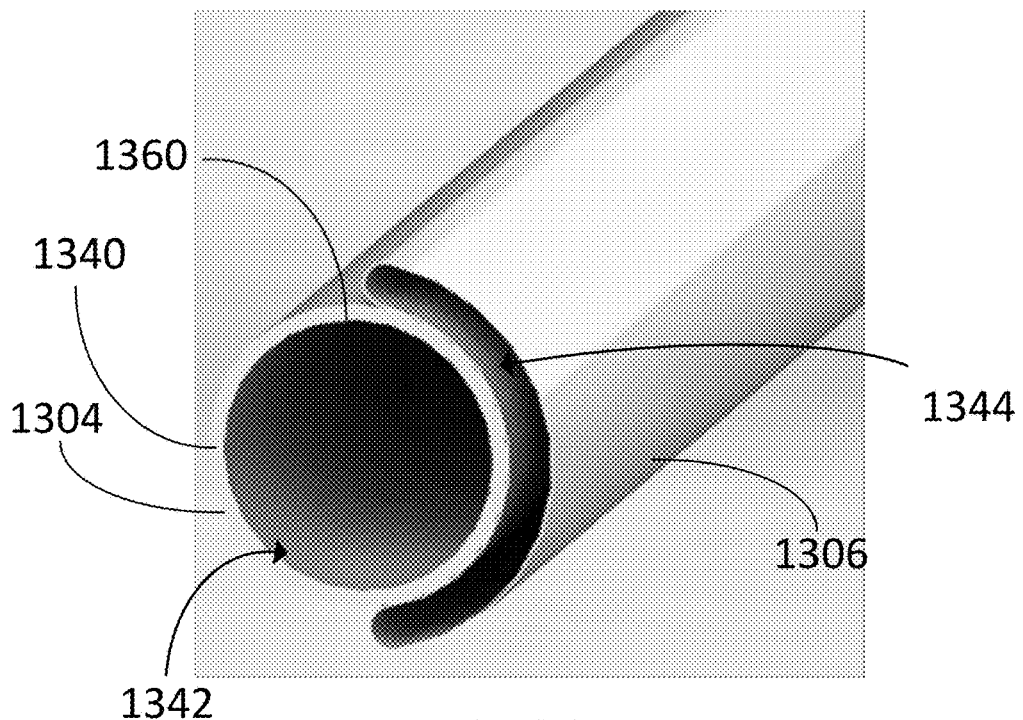
FIG. 20A is a perspective view of a vacuum tube and a balloon that can be used with the removal device of FIG. 1.
Figure 20B:
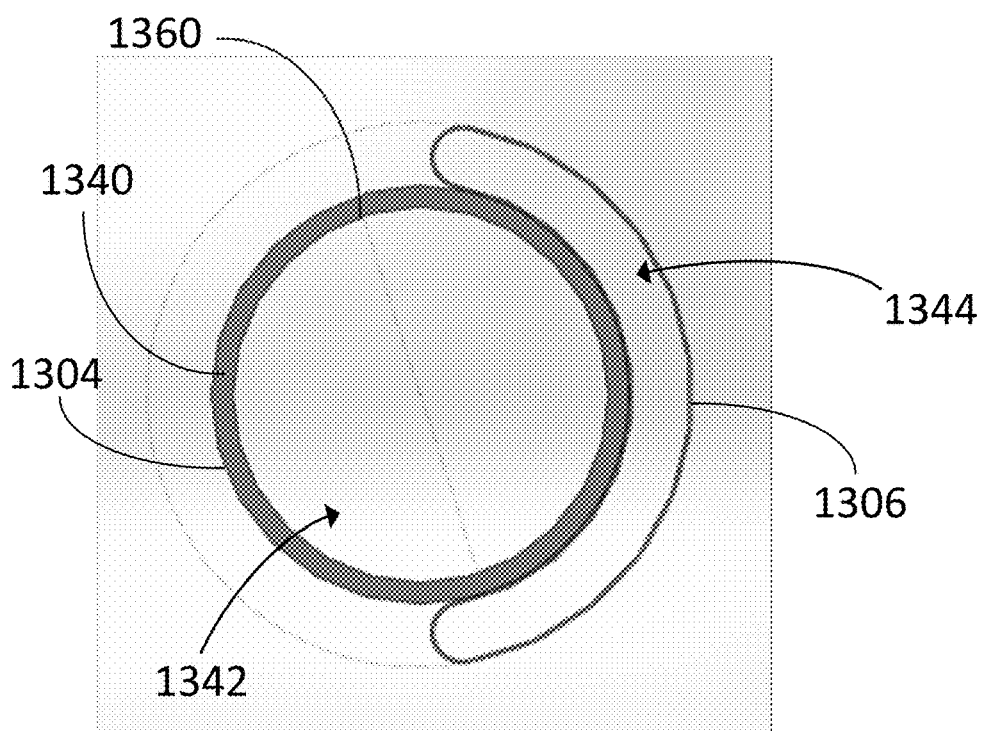
FIG. 20B is a front elevational view of the vacuum tube of FIG. 20A.

FIGS. 20A and 20B show a configuration of a vacuum tube 1304 that can be used in connection with the removal device 100. As shown in FIGS. 20A and 20B, the vacuum tube 1304 can be characterized by an elongate lumen 1340 defined by a first passageway 1342 extending longitudinally therethrough, and can be used in connection with a second passageway 1344 defined by a collapsible balloon 1306 extending adjacent to vacuum tube 1304. The second passageway 1344 can be disposed adjacent an external surface of the vacuum tube 1304. For example, as illustrated, the second passageway 1344 can be disposed to run along an exterior surface of vacuum tube 1304. In one configuration, the first passageway 1342 can be used to accommodate suction from the suction source 148 (e.g., as described above in connection with FIG. 6).

Still referencing FIGS. 20A and 20B, the first passageway 1342 of the vacuum tube 1304 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the second passageway 1344 can accommodate the flow of an irrigation fluid from a fluid irrigation source to a distal end of the vacuum tube 1304 to facilitate the removal of debris through an in vivo passageway of a patient. For example, in one particular non-limiting configuration, the fluid irrigation source can be a syringe connected through any suitable connection, such as a needle that is in fluid communication with the second passageway 1344, a luer-type connector that is in fluid communication with the second passageway 1344, and/or any other suitable connector. Pressure can be applied to the syringe to dispense the irrigation fluid through the second passageway 1344 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art. In some configurations, when the second passageway 1344 is not receiving irrigation fluid it can collapse against the vacuum tube 1304. In some embodiments, balloon 1306 can be any suitable material or combination of materials, such as polyethylene terephthalate (PET), polyether block amide (PEBA) such as Pebax®, nylon, polyethylene (PE), polyurethane, polyether ether ketone (PEEK), silicone, etc.

The vacuum tube 1304 can be configured to selectively provide suction (e.g., through the first passageway 1342) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1304.

The first passageway 1342 and the second passageway 1344 can be configured to be any suitable sizes. For example, in one non-limiting configuration, the first passageway 1342 can have an internal diameter of about 3.0 millimeters, and the second passageway 1344 can have a cross-sectional area of about 2.6265 square millimeters.

Figure 21A:
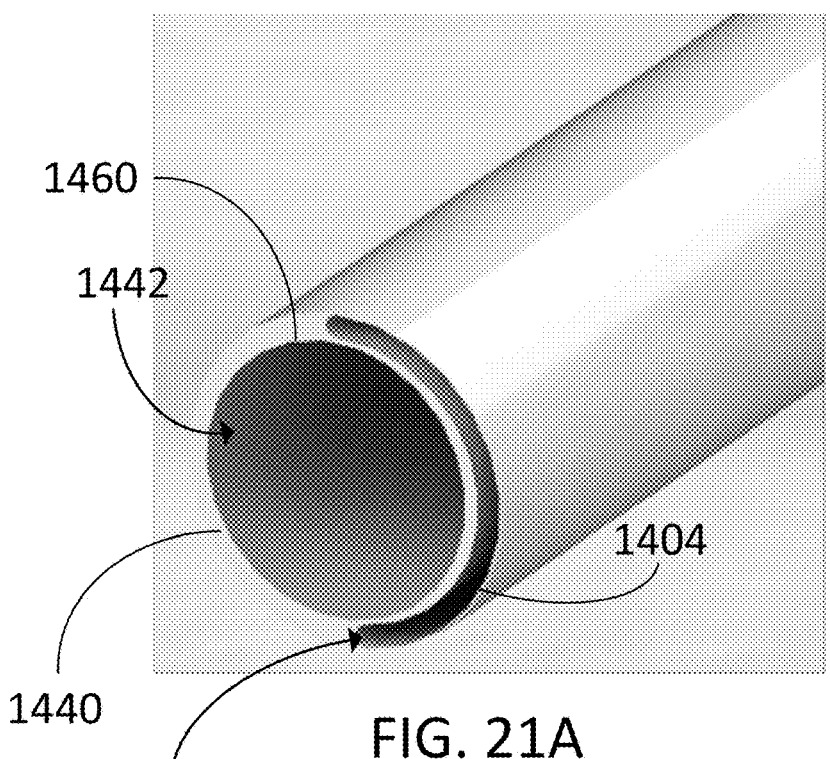
FIG. 21A is a perspective view of a dual lumen vacuum tube with a peripheral passageway that can be used with the removal device of FIG. 1.
Figure 21B:
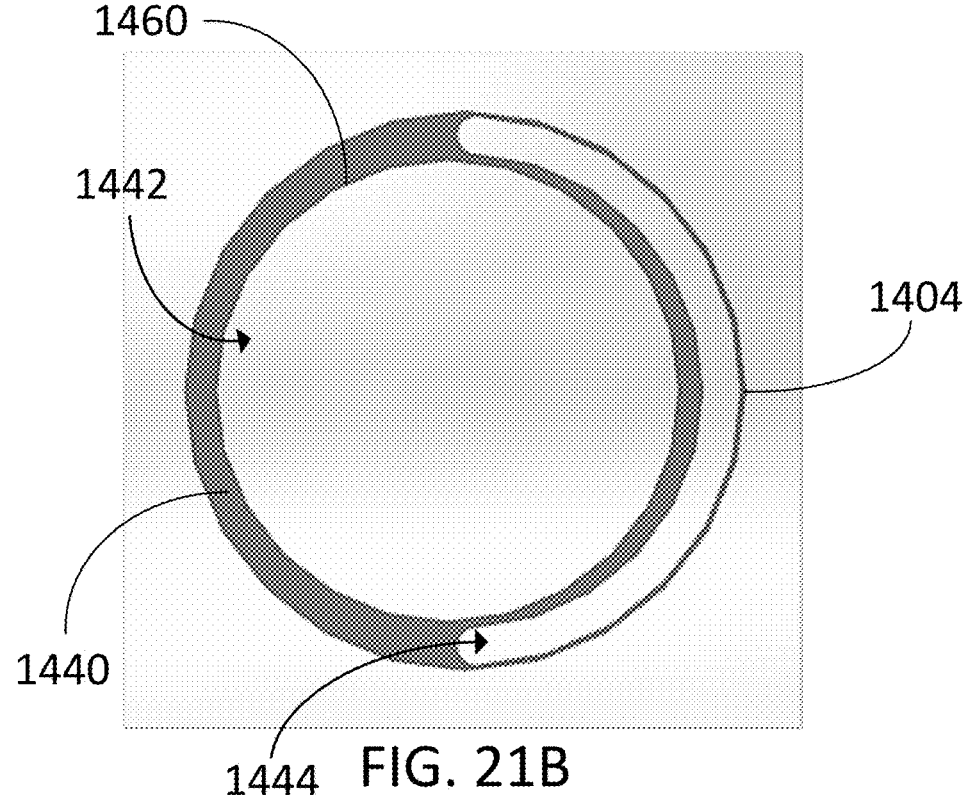
FIG. 21B is a front elevational view of the vacuum tube of FIG. 21A.

FIGS. 21A and 21B show a configuration of a vacuum tube 1404 that can be used in connection with the removal device 100. As shown in FIGS. 21A and 21B, the vacuum tube 1404 can be characterized by an elongate lumen 1440 defined by a first passageway 1442 and a second passageway 1444 extending longitudinally therethrough. The second passageway 1444 can be formed within a wall of vacuum tube 1404 between an internal surface 1460 and an external surface of the vacuum tube 1404. In one configuration, the first passageway 1442 can be used to accommodate suction from the suction source 148 (e.g., as described above in connection with FIG. 6).

Still referencing FIGS. 21A and 21B, the first passageway 1442 of the vacuum tube 1404 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the second passageway 1444 can accommodate the flow of an irrigation fluid from a fluid irrigation source to a distal end of the vacuum tube 1404 to facilitate the removal of debris through an in vivo passageway of a patient. For example, in one particular non-limiting configuration, the fluid irrigation source can be a syringe connected through any suitable connection, such as a needle that is in fluid communication with the second passageway 1444 of the vacuum tube 1404, a luer-type connector that is in fluid communication with the second passageway 1444 of the vacuum tube 1404, and/or any other suitable connector. Pressure can be applied to the syringe to dispense the irrigation fluid through the second passageway 1444 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art. In some configurations, when the second passageway 1444 is not receiving irrigation fluid it can collapse against the interior wall of vacuum tube 1404. In some embodiments, vacuum tube 1404 can be any suitable material or combination of materials, such as, PET, PEBA, nylon, PE, polyurethane, PEEK, silicone, etc.

The vacuum tube 1404 can be configured to selectively provide suction (e.g., through the first passageway 1442) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1404.

The first passageway 1442 and the second passageway 1444 can be configured to be any suitable sizes. For example, in one non-limiting configuration, the first passageway 1442 can have an internal diameter of about 3.0 millimeters, and the second passageway 1444 can have a cross-sectional area of about 1.341 square millimeters when inflated.

Figure 22A:
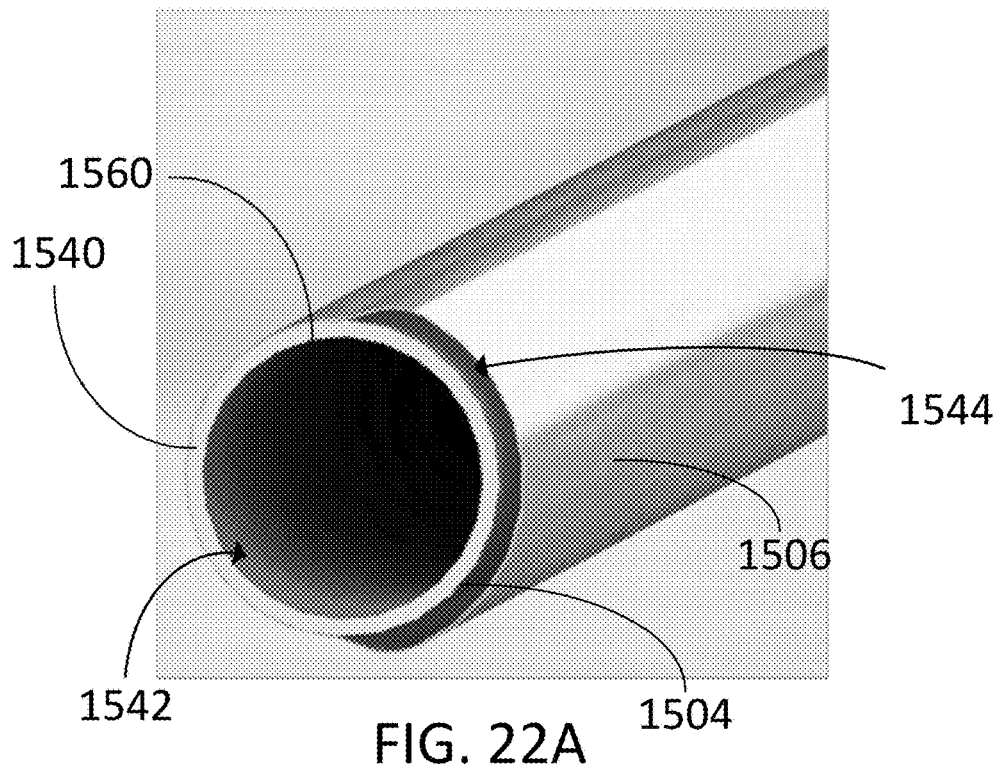
FIG. 22A is a perspective view of another vacuum tube and balloon that can be used with the removal device of FIG. 1.
Figure 22B:
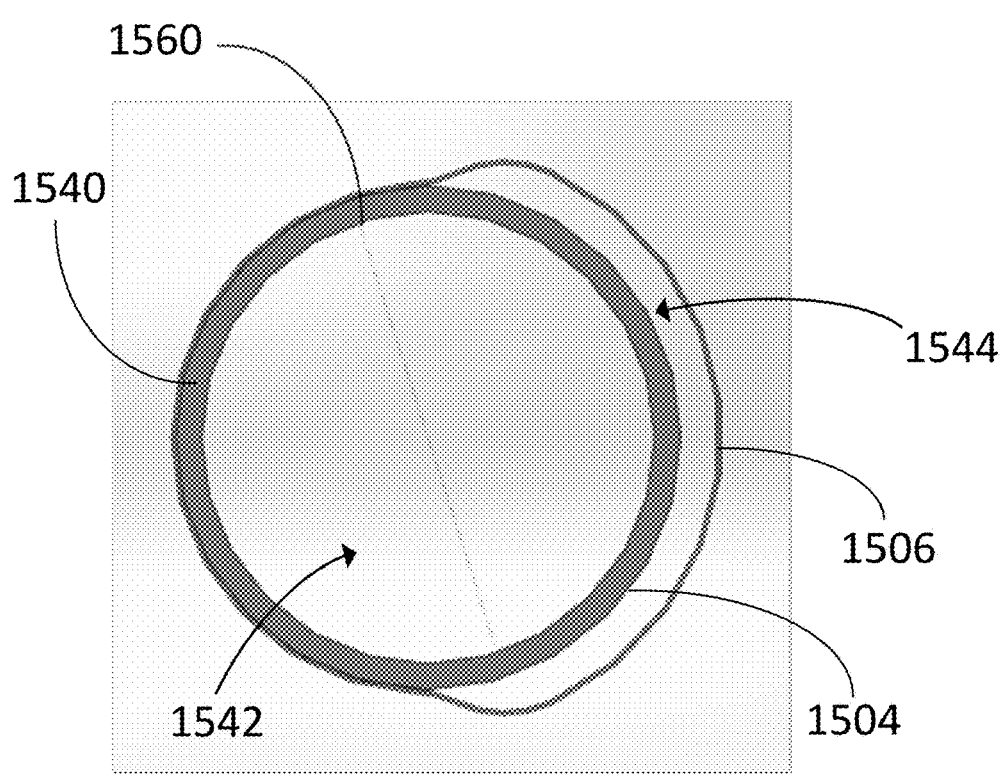
FIG. 22B is a front elevational view of the vacuum tube of FIG. 22A.

FIGS. 22A and 22B show a configuration of a vacuum tube 1504 that can be used in connection with the removal device 100. As shown in FIGS. 22A and 22B, the vacuum tube 1504 can be characterized by an elongate lumen 1540 defined by a first passageway 1542 extending longitudinally therethrough, and can be used in connection with a second passageway 1544 defined by a collapsible balloon 1506 that surrounds the vacuum tube 1504 and is bonded to at least a portion of an exterior surface of the vacuum tube 1504. The second passageway 1544 can be formed between the exterior surface of the vacuum tube 1504 and the balloon 1506. In one configuration, the first passageway 1542 can be used to accommodate suction from the suction source 148 (e.g., as described above in connection with FIG. 6).

Still referencing FIGS. 22A and 22B, the first passageway 1542 of the vacuum tube 1504 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the second passageway 1544 can accommodate the flow of an irrigation fluid from a fluid irrigation source to a distal end of the vacuum tube 1504 to facilitate the removal of debris through an in vivo passageway of a patient. For example, in one particular non-limiting configuration, the fluid irrigation source can be a syringe connected through any suitable connection, such as a needle that is in fluid communication with the second passageway 1544, a luer-type connector that is in fluid communication with the second passageway 1544, and/or any other suitable connector. Pressure can be applied to the syringe to dispense the irrigation fluid through the second passageway 1544 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art. In some configurations, when the second passageway 1544 is not receiving irrigation fluid it can at least partially collapse against the vacuum tube 1504. In some embodiments, balloon 1506 can be any suitable material or combination of materials, such as, PET, PEBA, nylon, PE, polyurethane, PEEK, silicone, etc.

The vacuum tube 1504 can be configured to selectively provide suction (e.g., through the first passageway 1542) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1504.

The first passageway 1542 and the second passageway 1544 can be configured to be any suitable sizes. For example, in one non-limiting configuration, the first passageway 1542 can have an internal diameter of about 3.0 millimeters, and the second passageway 1544 can have a cross-sectional area of about 1.2831 square millimeters.

Figure 23A:
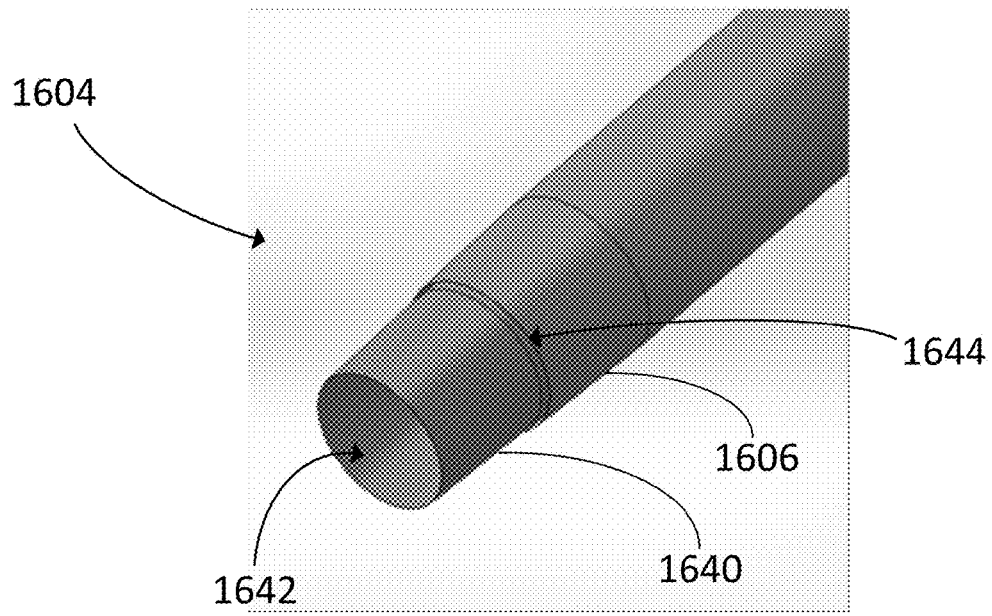
FIG. 23A is a perspective view of a tube in tube configuration for a vacuum tube with an annular gap that can be used with the removal device of FIG. 1.
Figure 23B:
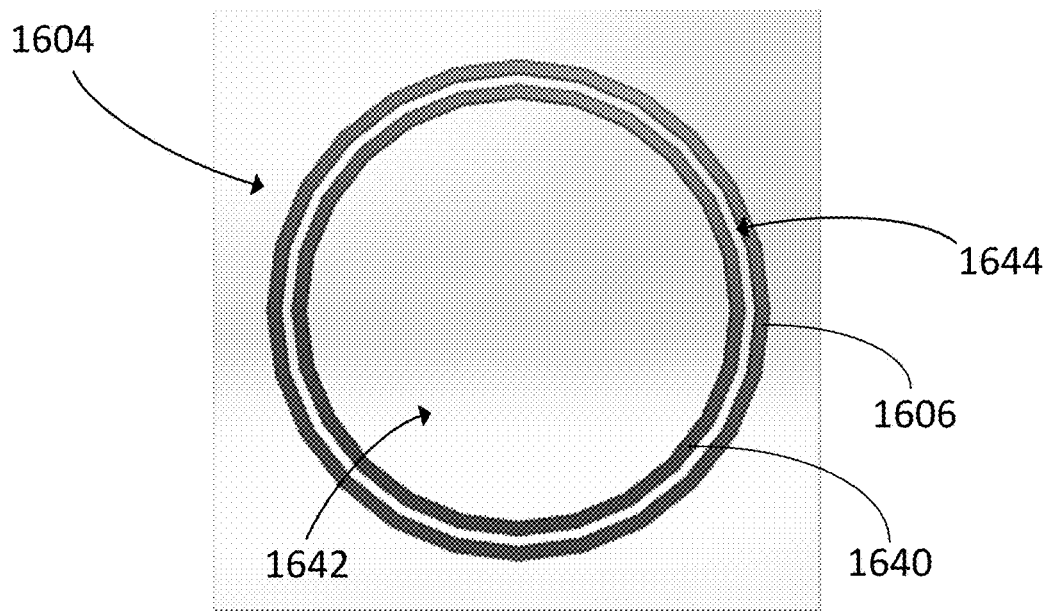
FIG. 23B is a front elevational view of the vacuum tube of FIG. 23A.

FIGS. 23A and 23B show a configuration of a dual lumen vacuum tube 1604 that can be used in connection with the removal device 100. As shown in FIGS. 23A and 23B, the vacuum tube 1604 can be characterized by a first elongate lumen 1640 defined by a first passageway 1642 extending longitudinally therethrough, and a second elongate lumen 1606 defined by a second passageway 1644 extending longitudinally therethrough that surrounds the first elongate lumen 1640. The second passageway 1644 can be formed between an exterior surface of the first elongate lumen 1640 and an interior surface of the second elongate lumen 1606. In one configuration, the first passageway 1642 can be used to accommodate suction from the suction source 148 (e.g., as described above in connection with FIG. 6). As illustrated, in some configurations, the first elongate lumen 1640 can extend past the end of the second elongate lumen 1606. Additionally, in some configurations, the first elongate lumen 1640 and/or the second elongate lumen 1606 can be tapered at the distal end.

Still referencing FIGS. 23A and 23B, the first passageway 1642 of the vacuum tube 1604 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the second passageway 1644 can accommodate the flow of an irrigation fluid from a fluid irrigation source to a distal end of the vacuum tube 1604 to facilitate the removal of debris through an in vivo passageway of a patient. For example, in one particular non-limiting configuration, the fluid irrigation source can be a syringe connected through any suitable connection, such as a needle that is in fluid communication with the second passageway 1644, a luer-type connector that is in fluid communication with the second passageway 1644, and/or any other suitable connector. Pressure can be applied to the syringe to dispense the irrigation fluid through the second passageway 1644 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 1604 can be configured to selectively provide suction (e.g., through the first passageway 1642) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1604.

The first passageway 1642 and the second passageway 1644 can be configured to be any suitable sizes. For example, in one non-limiting configuration, the first passageway 1642 can have an internal diameter of about 3.0 millimeters, and an annular gap between the first elongate lumen 1640 and the second elongate lumen 1606 can create a cross-sectional area of the second passageway of about 0.7949 square millimeters. In some embodiments, the first elongate lumen 1640 and/or the second elongate lumen 1606 can be made from any suitable material or combination of materials. For example, in some embodiments, the first elongate lumen 1640 can be made from a combination of materials that are more flexible (e.g., having a relatively lower durometer) closer to the end that is inserted through the subject's ureter (i.e., the distal end), and more stiff (e.g., having a higher durometer) closer to the end at which suction and/or irrigation is provided (i.e., the proximal end). In such an example, the distal end of the first elongate lumen 1640 can be a relatively low durometer material such as a relatively flexible polyurethane, PEBA, etc., and the proximal end of the first elongate lumen 1640 can be a relatively high durometer material such as a relatively stiff polyurethane, PEBA, polyamide, PEEK, stainless steel, etc. As another example, the first elongate lumen 1640 can be a laminate of different materials, such as polyamide and PEBA in which the thickness and/or durometer of one or both of the materials can be varied along the length of the first elongate lumen to produce a stiffer proximal portion and a more flexible distal portion. In some embodiments, the second lumen 1606 can be any suitable material or combination of materials. For example, the second lumen 1606 can be a relatively flexible (e.g., relatively low durometer) material, such as polyurethane, PEBA, etc.

In some embodiments, the first elongate lumen 1640 and/or the second elongate lumen 1606 can encapsulate a reinforcement element (not shown). For example, the reinforcement mechanism can be a coil, a braid, a combination of coil and braid, a braid over a coil, etc. In some embodiments, the reinforcement element can be made from any suitable material or combination of materials, such as stainless steel, copper, textile, etc. In some embodiments, the reinforcement element can inhibit kinking of the first elongate lumen 1640 and/or the second elongate lumen 1606, when, for example, the vacuum tube 1604 is navigated around a tight radius of curvature.

Figure 24A:
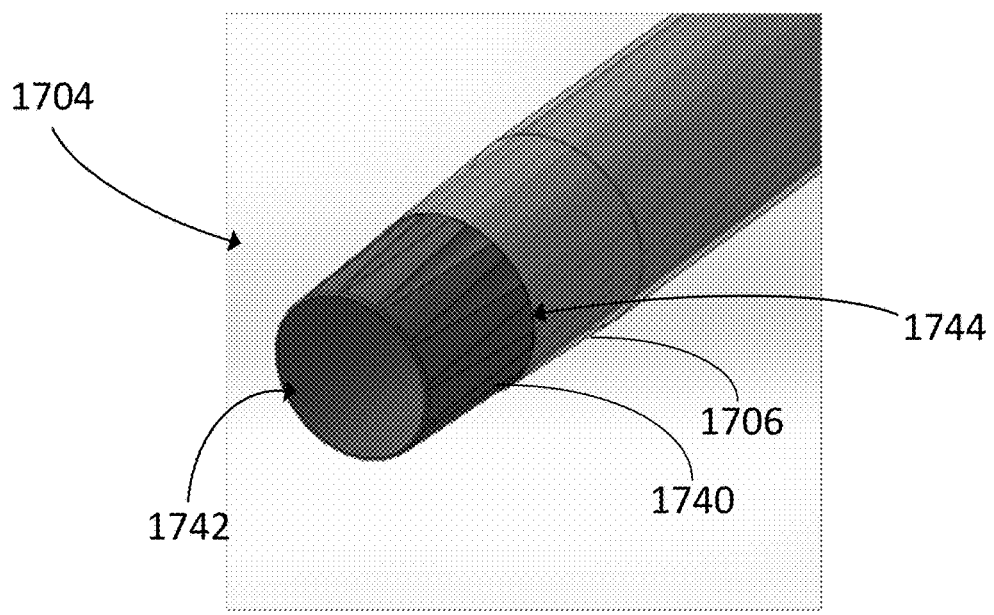
FIG. 24A is a perspective view of a tube in tube configuration for a vacuum tube with peripheral passageways that can be used with the removal device of FIG. 1.
Figure 24B:
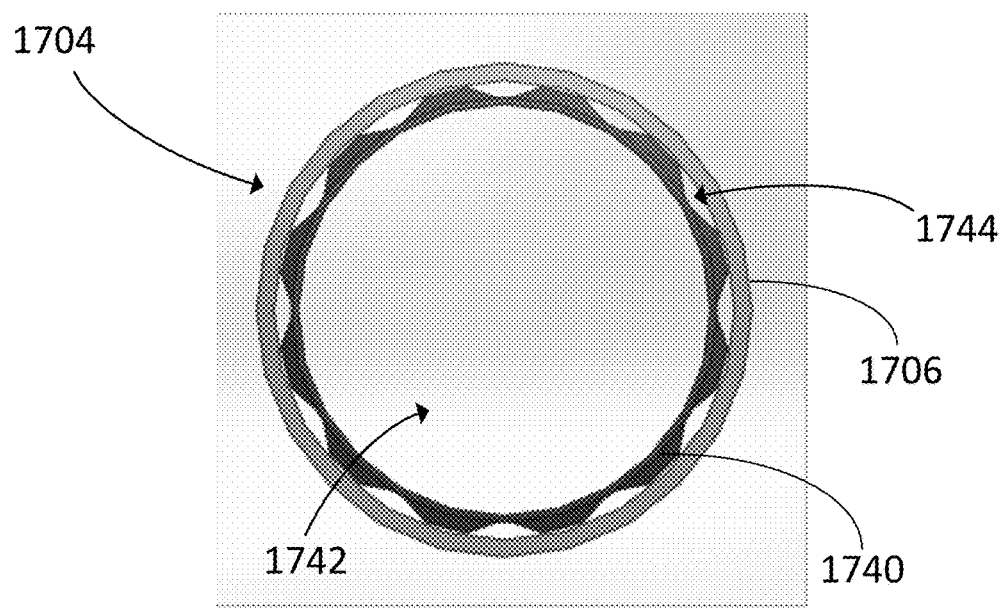
FIG. 24B is a front elevational view of the vacuum tube of FIG. 24A.

FIGS. 24A and 24B show a configuration of a dual lumen vacuum tube 1704 that can be used in connection with the removal device 100. As shown in FIGS. 24A and 24B, the vacuum tube 1704 can be characterized by a first elongate lumen 1740 defined by a first passageway 1742 extending longitudinally therethrough and an exterior surface that is fluted to form a series of ridges, and a second elongate lumen 1706 with an interior surface that contacts the ridges of the first elongate lumen and defines many peripheral passageways 1744 that surround the first elongate lumen 1740. As illustrated, the peripheral passageways 1744 can be formed between the ridged exterior surface of the first elongate lumen 1740 and an interior surface of the second elongate lumen 1706. In one configuration, the first passageway 1742 can be used to accommodate suction from the suction source 148 (e.g., as described above in connection with FIG. 6). As illustrated, in some configurations, the first elongate lumen 1740 can extend past the end of the second elongate lumen 1706. Additionally, in some configurations, the first elongate lumen 1740 and/or the second elongate lumen 1706 can be tapered at the distal end.

Still referencing FIGS. 24A and 24B, the first passageway 1742 of the vacuum tube 1704 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the peripheral passageways 1744 can accommodate the flow of an irrigation fluid from a fluid irrigation source to a distal end of the vacuum tube 1704 to facilitate the removal of debris through an in vivo passageway of a patient. For example, in one particular non-limiting configuration, the fluid irrigation source can be a syringe connected through any suitable connection, such as a needle that is in fluid communication with the peripheral passageways 1744, a luer-type connector that is in fluid communication with the peripheral passageways 1744, and/or any other suitable connector. Pressure can be applied to the syringe to dispense the irrigation fluid through the second passageway 1744 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 1704 can be configured to selectively provide suction (e.g., through the first passageway 1742) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1704.

The first passageway 1742 and the peripheral passageways 1744 can be configured to be any suitable sizes. For example, in one non-limiting configuration, the first passageway 1742 can have an internal diameter of about 2.99 millimeters, and gaps between the first elongate lumen 1740 and the second elongate lumen 1706 can create a combined cross-sectional area of the peripheral passageways of about 0.7131 square millimeters. Although the ridges on the exterior surface of the first elongate lumen 1740 are shown extending parallel to a central axis of the first elongate lumen, each ridge can be configured to extend along the length of the first elongate lumen 1740 with any suitable shape, such as to form a series of helical ridges that extend the length of the first elongate lumen 1740. In some embodiments, the first elongate lumen 1740 and/or the second elongate lumen 1706 can be made from any suitable materials and/or any suitable characteristics (e.g., stiffness, reinforcement, etc.), such as materials and characteristics described above in connection with FIGS. 23A and 23B.

Figure 25A:
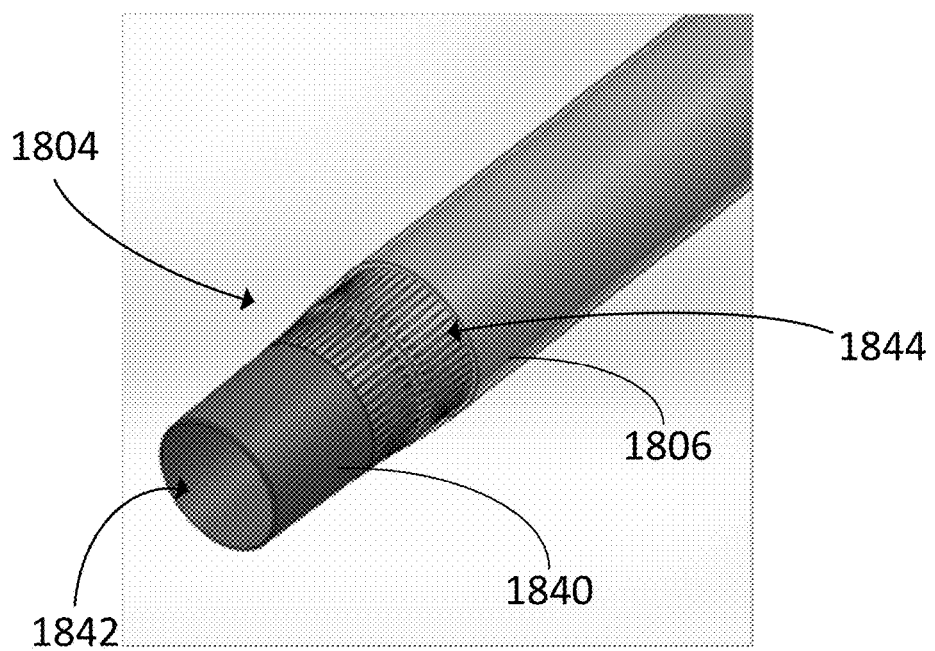
FIG. 25A is a perspective view of another tube in tube configuration for a vacuum tube with peripheral passageways that can be used with the removal device of FIG. 1.
Figure 25B:
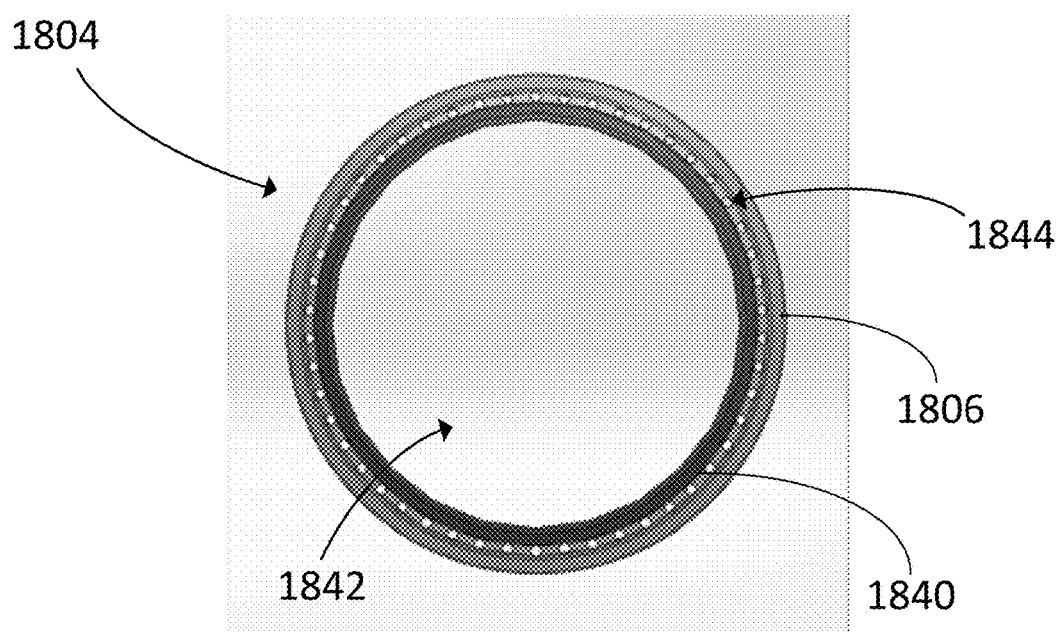
FIG. 25B is a front elevational view of the vacuum tube of FIG. 25A.

FIGS. 25A and 25B show a configuration of a dual lumen vacuum tube 1804 that can be used in connection with the removal device 100. As shown in FIGS. 25A and 25B, the vacuum tube 1804 can be characterized by a first elongate lumen 1840 defined by a first passageway 1842 extending longitudinally therethrough, and a second elongate lumen 1806. As illustrated in FIGS. 25A and 25B, interstitial material can be placed and/or formed between an interior surface of the second elongate lumen 1806 and an exterior surface of the first elongate lumen 1840 to define many peripheral passageways 1844 that surround the first elongate lumen 1840. The interstitial material can be formed as a portion of the first elongate lumen 1840, formed as a portion of the second elongate lumen 1806, formed separately and bonded to the first elongate lumen 1840 and/or the second elongate lumen 1806, and/or any suitable combination thereof. In one configuration, the first passageway 1842 can be used to accommodate suction from the suction source 148 (e.g., as described above in connection with FIG. 6). As illustrated, in some configurations, the first elongate lumen 1840 can extend past the end of the second elongate lumen 1806. Additionally, in some configurations, the first elongate lumen 1840 and/or the second elongate lumen 1806 can be tapered at the distal end.

Still referencing FIGS. 25A and 25B, the first passageway 1842 of the vacuum tube 1804 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the peripheral passageways 1844 can accommodate the flow of an irrigation fluid from a fluid irrigation source to a distal end of the vacuum tube 1804 to facilitate the removal of debris through an in vivo passageway of a patient. For example, in one particular non-limiting configuration, the fluid irrigation source can be a syringe connected through any suitable connection, such as a needle that is in fluid communication with the peripheral passageways 1844, a luer-type connector that is in fluid communication with the peripheral passageways 1844, and/or any other suitable connector. Pressure can be applied to the syringe to dispense the irrigation fluid through the second passageway 1844 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 1804 can be configured to selectively provide suction (e.g., through the first passageway 1842) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1804.

The first passageway 1842 and the peripheral passageways 1844 can be configured to be any suitable sizes. For example, in one non-limiting configuration, the first passageway 1842 can have an internal diameter of about 2.94 millimeters, and the peripheral passageways 1844 can have a combined cross-sectional area of about 0.228 square millimeters. Although the peripheral passageways 1844 are shown extending parallel to a central axis of the first elongate lumen, the peripheral passageways can be configured to extend along the length of the vacuum tube 1804 with any suitable shape, such as to form a series of helical passageways.

In some embodiments, the first lumen 1840 and the second lumen 1806 can be any suitable material or combination of materials. For example, in some embodiments, the first lumen 1840 can be PEBA, and the second lumen 1806 can be polyurethane, or vice versa. In some embodiments, the peripheral passageways 1844 can be formed by inserting mandrels between the first lumen 1840 and the second lumen 1806 and heating the first lumen 1840 and the second lumen 1806 to a temperature at which the lumens flow together around the mandrels to bond the first lumen and the second lumen around the mandrels. In such embodiments, the mandrels can be removed to leave the peripheral passageways 1844 clear to be used to transport fluid to the distal end of the vacuum tube 1804. In some embodiments, the peripheral passageways can run through the entire length of the vacuum tube 1804. Alternatively, the peripheral passageways 1844 can run through only a portion of the vacuum tube, such as a portion near the distal end of the vacuum tube 1804, and an annular gap between the first lumen 1840 and the second lumen 1806 can form a passageway for fluid in the bulk of the vacuum tube 1804.

Figure 26A:
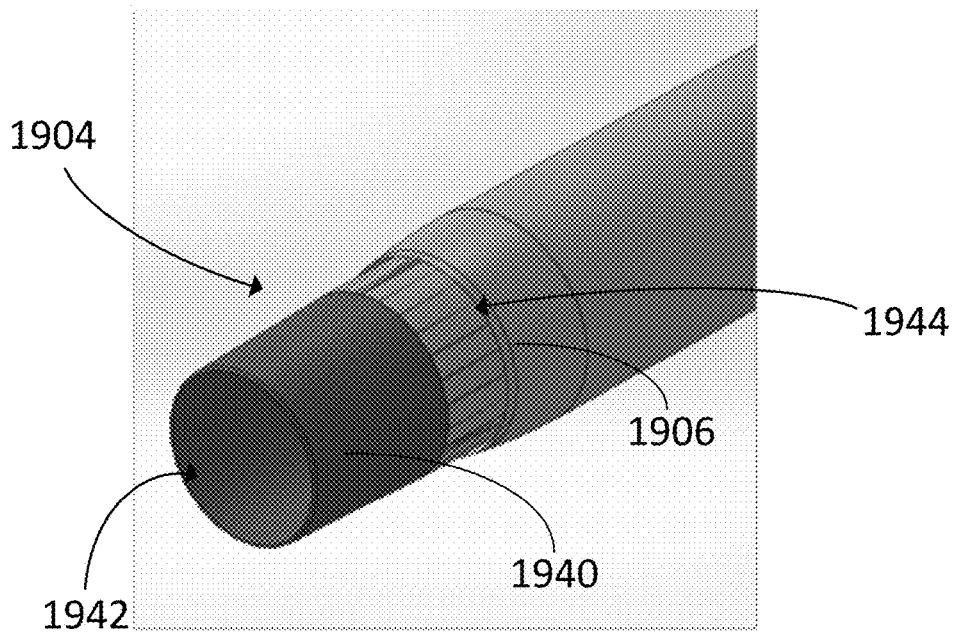
FIG. 26A is a perspective view of yet another tube in tube configuration for a vacuum tube with peripheral passageways that can be used with the removal device of FIG. 1.
Figure 26B:
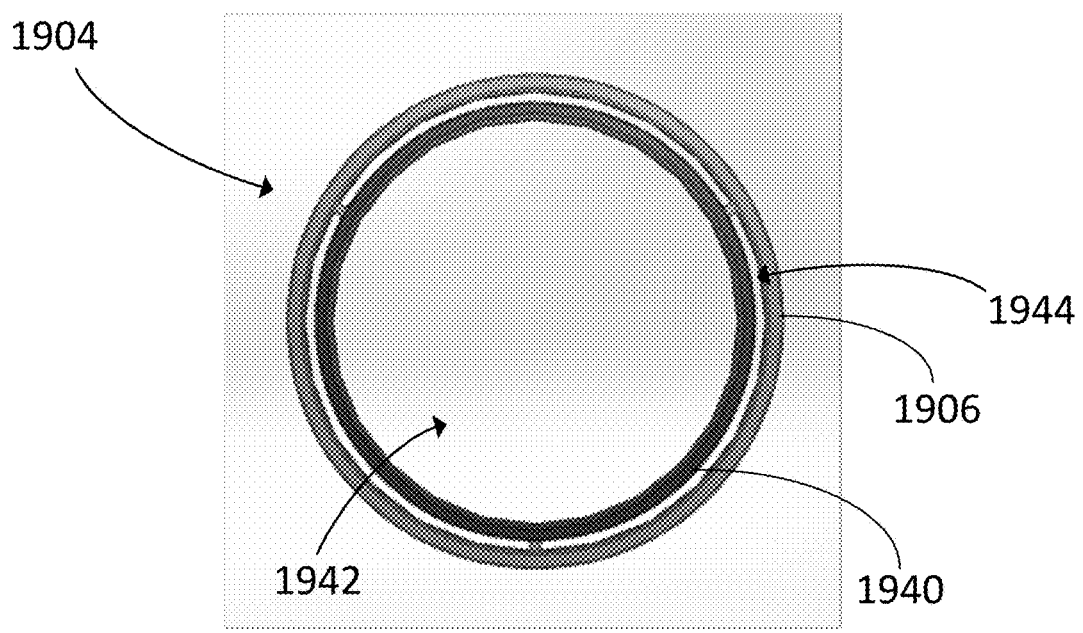
FIG. 26B is a front elevational view of the vacuum tube of FIG. 26A.

FIGS. 26A and 26B show a configuration of a dual lumen vacuum tube 1904 that can be used in connection with the removal device 100. As shown in FIGS. 26A and 26B, the vacuum tube 1904 can be characterized by a first elongate lumen 1940 defined by a first passageway 1942 extending longitudinally therethrough, and a second elongate lumen 1906. As illustrated in FIGS. 26A and 26B, interstitial material can be placed and/or formed between an interior surface of the second elongate lumen 1906 and an exterior surface of the first elongate lumen 1940 to define three peripheral passageways 1944 that surround the first elongate lumen 1940. The interstitial material can be formed as a portion of the first elongate lumen 1940, formed as a portion of the second elongate lumen 1906, formed separately and bonded to the first elongate lumen 1940 and/or the second elongate lumen 1906, and/or any suitable combination thereof. In one configuration, the first passageway 1942 can be used to accommodate suction from the suction source 148 (e.g., as described above in connection with FIG. 6). As illustrated, in some configurations, the first elongate lumen 1940 can extend past the end of the second elongate lumen 1906. Additionally, in some configurations, the first elongate lumen 1940 and/or the second elongate lumen 1906 can be tapered at the distal end.

Still referencing FIGS. 26A and 26B, the first passageway 1942 of the vacuum tube 1904 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the peripheral passageways 1944 can accommodate the flow of an irrigation fluid from a fluid irrigation source to a distal end of the vacuum tube 1904 to facilitate the removal of debris through an in vivo passageway of a patient. For example, in one particular non-limiting configuration, the fluid irrigation source can be a syringe connected through any suitable connection, such as a needle that is in fluid communication with the peripheral passageways 1944, a luer-type connector that is in fluid communication with the peripheral passageways 1944, and/or any other suitable connector. Pressure can be applied to the syringe to dispense the irrigation fluid through the peripheral passageways 1944 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 1904 can be configured to selectively provide suction (e.g., through the first passageway 1942) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1904.

The first passageway 1942 and the peripheral passageways 1944 can be configured to be any suitable sizes. For example, in one non-limiting configuration, the first passageway 1942 can have an internal diameter of about 2.94 millimeters, and the peripheral passageways 1944 can have a combined cross-sectional area of about 0.7638 square millimeters. Although the peripheral passageways 1944 are shown extending parallel to a central axis of the first elongate lumen, the peripheral passageways 1944 can be configured to extend along the length of the vacuum tube 1904 with any suitable shape, such as to form a series of helical passageways.

Figure 27A:
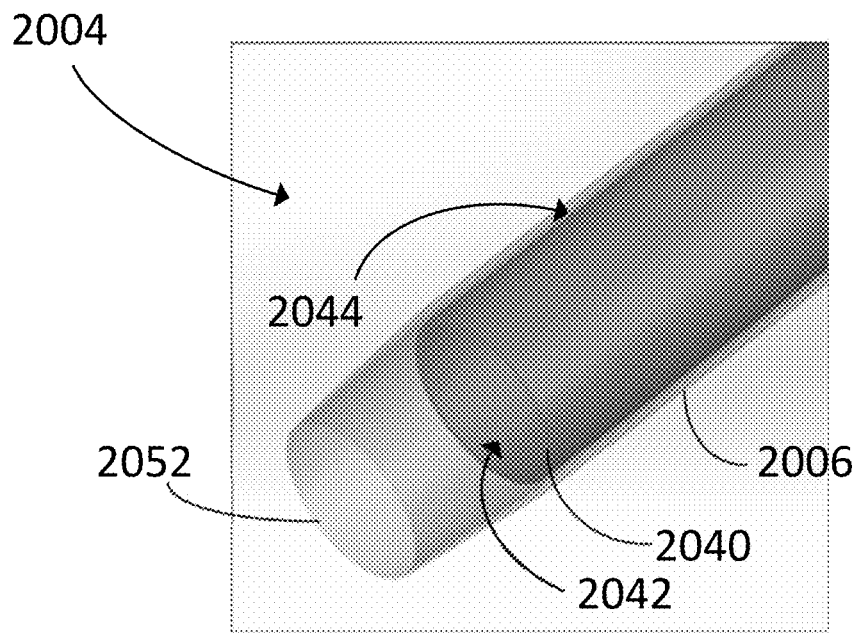
FIG. 27A is an isometric view of another tube in tube configuration for a vacuum tube with an annular gap that can be used with the removal device of FIG. 1.
Figure 27B:
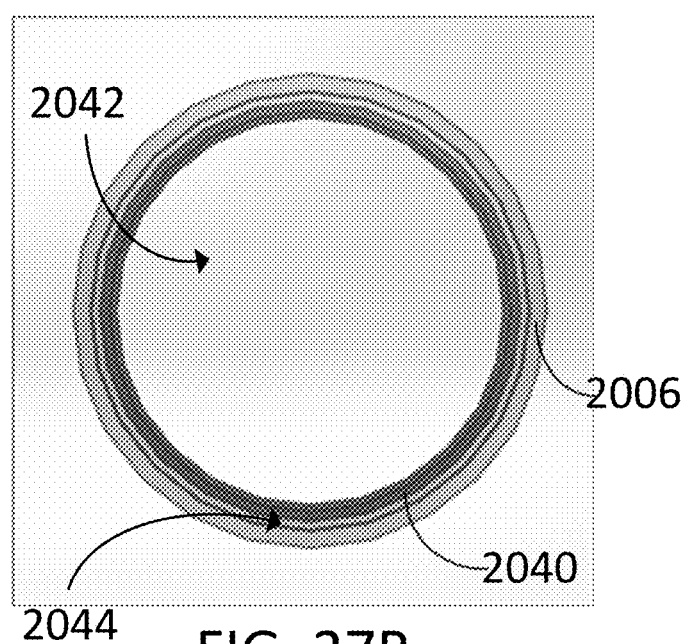
FIG. 27B is a front elevational view of the vacuum tube of FIG. 27A.

FIGS. 27A and 27B show a configuration of a dual lumen vacuum tube 1904 that can be used in connection with the removal device 100. As shown in FIGS. 26A and 26B the vacuum tube 2004 can be characterized by a first elongate lumen 2040 defined by a first passageway 2042 extending longitudinally therethrough and a second elongate lumen 2006. The second elongate lumen 2006 can include a nozzle tip 2052 that is tapered toward a central axis of the first elongate lumen 2040 such that the first elongate lumen 2040 is held and maintained within the second elongate lumen 2006. The vacuum tube 2004 further includes a first passageway 2042 and a second passageway 2044 extending longitudinally therethrough.

Still referencing FIGS. 27A and 27B, the first passageway 2042 of the vacuum tube 2004 can be configured to accommodate the navigation mechanism 106 (e.g., a guidewire) and/or another device (e.g., ureteroscope 134, another viewing instrument, etc.). In such a configuration, the navigation mechanism 106 and/or another device can be removed from the first passageway prior to providing suction or left in place while suction is provided. In some configurations, the second passageway 2044 can accommodate the flow of an irrigation fluid from a fluid irrigation source to a distal end of the vacuum tube 2004 to facilitate the removal of debris through an in vivo passageway of a patient. For example, in one particular non-limiting configuration, the fluid irrigation source can be a syringe connected through any suitable connection, such as a needle that is in fluid communication with the second passageway 2044, a luer-type connector that is in fluid communication with the peripheral passageways 2044, and/or any other suitable connector. Pressure can be applied to the syringe to dispense the irrigation fluid through the second passageway 2044 in the direction of the object to be removed. In other non-limiting examples, in addition to, and/or in lieu of, the syringe described above, the fluid irrigation source can include a wash bottle, a positive displacement pump, or any other suitable fluid irrigation sources known to those skilled in the art.

The vacuum tube 2004 can be configured to selectively provide suction (e.g., through the first passageway 2042) from the suction source (e.g., suction source 148 described above in connection with FIGS. 1-8) before, during and/or after flushing a target region of the in vivo passageway with the irrigation fluid. For example, as described above, the valve 110 (as shown in FIG. 6) can be used to control suction that is supplied to the vacuum tube 1904.

The first passageway 2042 and the second passageway 2044 can be configured to be any suitable sizes. For example, in one non-limiting configuration, the first passageway 2042 can have an internal diameter of about 2.94 millimeters, and the second passageway 2044 can have a cross-sectional area of about 0.7828 square millimeters as an annular region around the first lumen 2040. In some embodiments, the nozzle tip 2052 of the second lumen 2006 can have an internal diameter that is the same or smaller than the internal diameter of the first passageway 2042 (e.g., less than or equal to 2.94 mm).

The vacuum tubes described in connection with FIGS. 9A to 27B can be made from any suitable materials, such as flexible biocompatible materials. In some embodiments, this can facilitate movement of the vacuum tubes through the contours of the in vivo passageway(s) of the patient. Examples of compatible materials are described above. In some non-limiting configurations, one or more portions of the vacuum tubes described herein can include a coating and/or can include one or more hydrophilic or hydrophobic materials to assist in positioning the vacuum tube within the sheath (and/or an in vivo passageway of the patient), positioning the navigation mechanism within the vacuum tube, and/or assisting in debris removal through the first passageway.

Figure 28A:
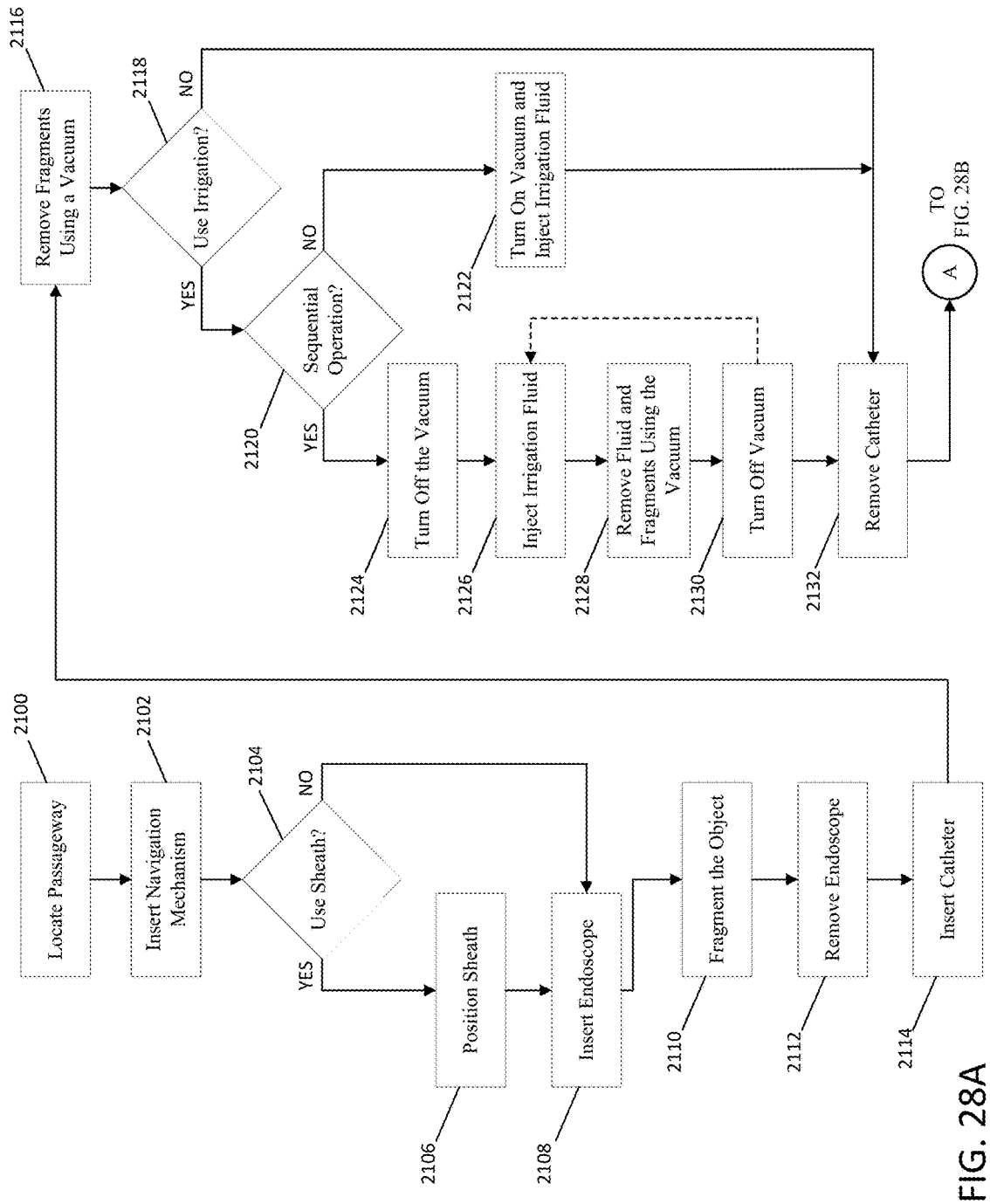
FIGS. 28A and 28B show an example of a flow chart setting forth some examples of steps in a process for removing an object from a passageway using the removal device described herein.
Figure 28B:
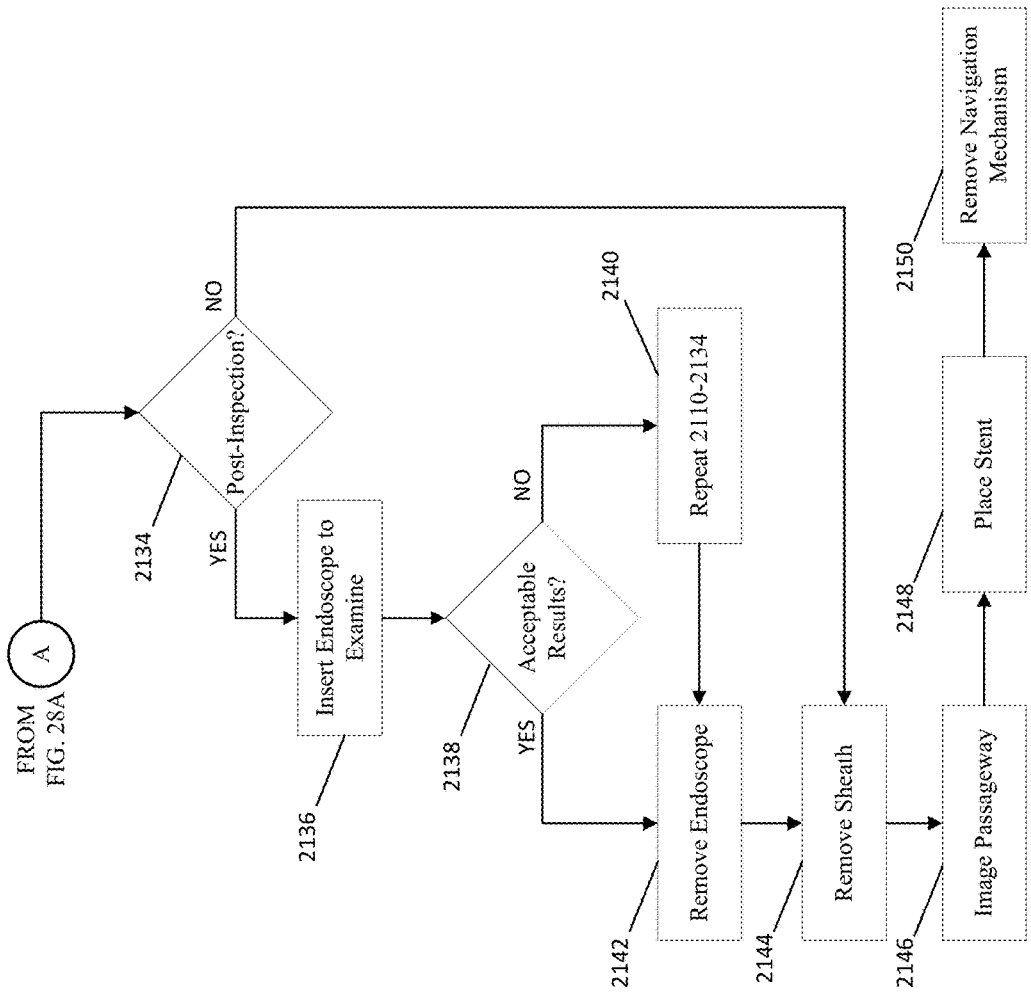

Operation of the removal device 100 when removing a kidney stone 118 from a patient's kidney 116 through the patient's ureter 112 is described below with reference to FIGS. 28A and 28B. The removal device 100 can include any suitable configuration, such as configurations described above in connection with FIGS. 1 to 27B. Additionally or alternatively, in some configurations, the removal device 100 can be configured for other medical uses such as treating bladder stones, and/or for use with other procedures, such as percutaneous stone removal, laparoscopic procedures, spine procedures, arthroscopic surgery, and microsurgery (e.g., to treat knee, ankle, foot, and hand issues). The removal device 100 can also be used to remove dead tissue, masses, and other debris. In a further configuration, the removal device 100 can be used in biopsy procedures.

At 2100, the removal device 100 can be configured to locate the passageway that contains the object for removal. In one non-limiting configuration, the passageway can be located using a cystoscope, which can be inserted into the bladder and used to find the opening to the patient's ureter 112.

At 2102, the navigation mechanism 106 can be inserted into the passageway 132 of the patient. In some configurations, the navigation mechanism 106 includes a guide wire that is inserted into the patient's ureter 112, and passed through to the patient's kidney 116. A sheath 102 can then be optionally positioned over the navigation mechanism. If the sheath 102 is being used in the procedure ("YES" at 2104), the sheath can be positioned in the patient's ureter 112 at 2106.

At 2108, an endoscope can be inserted into the passageway of the patient and positioned adjacent to the target object (e.g., a kidney stone). Note that the endoscope can be used regardless of whether the sheath is being used at 2104. In a non-limiting example, the endoscope can be a ureteroscope (e.g., the ureteroscope 134) that can be positioned adjacent to a kidney stone 118 within a patient's kidney 116.

At 2110, the endoscope can be used to fragment the object using any suitable technique or combination of techniques. For example, in some configurations, the ureteroscope includes a laser that can be used to break the kidney stone 118 into fragments until the fragments have reached a suitable sized, such as roughly 3 mm or smaller. It is to be appreciated that, in some configurations, the ureteroscope can be maneuvered without the assistance of the guide wire 106. At 2112, the endoscope can be removed from the patient's ureter 112 and/or from the sheath 102.

At 2114, a catheter can be inserted into the passageway of the patient and/or the sheath 102 of the removal device 100. In some configurations, the catheter can include multiple lumens. For example, as described above in connection with FIG. 3, the first lumen can be the first passageway 142 of vacuum tube 104, and the second lumen can be the second passageway 144, which can, among other things, accommodate the navigation mechanism 106, and/or can be in fluid communication with the irrigation fluid source. Alternatively, a variety of catheters with various configurations can be used, such as configurations described above in connection with FIGS. 9A to 27B. Note that, in some configurations, the catheter can be inserted through sheath 102 and/or the in vivo passageway of the patient and the endoscope can be inserted through the catheter. For example, as described above in connection with FIGS. 9A and 9B, the second passageway of the vacuum tube 204 can accommodate an appropriately sized endoscope (e.g., an endoscope having an external diameter less than or equal to about 1 millimeter). As another example, as described above in connection with FIGS. 17A and 17B, the first passageway 1042 of vacuum tube 1004 can accommodate an appropriately sized endoscope (e.g., an endoscope having an external diameter less than or equal to about 2.75 millimeters).

At 2116, the fragments within the passageway of the patient can be removed using the vacuum tube. In one non-limiting configuration, a fluoroscope may be used as a visual guide to position the vacuum adjacent to the fragments to be removed. In some configurations, an irrigation fluid can be used to assist in the removal of the fragments from the passageway 134. If irrigation is to be used ("YES" at 2118), in one non-limiting configuration, an irrigation fluid source (e.g., a syringe containing irrigation fluid, an IV bag containing irrigation fluid, etc.) can be coupled to at least one lumen of the catheter to place the irrigation fluid source into fluid communication with the at least one lumen in the catheter. If irrigation fluid is to be used, the suction and irrigation provided through the removal device 100 can be configured to operate sequentially ("YES" at 2120) or simultaneously ("NO" at 2120). If suction and irrigation are to be provided simultaneously ("NO" at 2120), at 2122, the valve 110 in fluid communication with the catheter can be opened to provide suction through a first lumen of the catheter (e.g., the first passageway 242 of the vacuum tube 204) during injection of the irrigation fluid through a second lumen of the catheter (e.g., the second passageway 244 of the vacuum tube 204). Alternatively, if suction and irrigation are to be provided sequentially ("YES" at 2120), at 2124, the valve 110 in fluid communication with the catheter can be closed and/or can remain closed while irrigation fluid is injected through the catheter, at 2126. In some embodiments, irrigation can be provided to the area from which objects are to be removed at any suitable rate of flow. In some cases, providing suction without irrigation can lead to tissue (e.g., kidney tissue) being aspirated into the vacuum tube, potentially inhibiting objects (e.g., kidney stones) from being aspirated by the vacuum tube. In some embodiments, irrigation fluid can be provided at any suitable flow rate. For example, in some embodiments, irrigation can be provided at 5 ml per minute to 100 ml per minute. As another example, in some embodiments, irrigation can be provided at 30 ml per minute to 75 ml per minute. As yet another example, in some embodiments, irrigation can be provided at 40 ml per minute to 65 ml per minute. As still another example, in some embodiments, irrigation can be provided at 45 ml per minute to 55 ml per minute. Providing irrigation at relatively high flow rates may not be effective at removing objects from kidneys without the use of suction, as the higher pressure may not allow the irrigation fluid to flow through the kidney in such a way that kidney stones are transported with the fluid into the catheter. Additionally, in some cases, providing irrigation at higher flow rates may result in reflux of fluid from the kidney. In some embodiments, the irrigation can be provided at a particular flow rate from any suitable source. For example, irrigation can be provided from an intravenous (IV) fluid bag, and flow can be controlled using any suitable technique or combination of techniques, such as a pressure cuff or a hand pump. In some embodiments, irrigation fluid can be provided at a flow rate sufficient to inhibit tissue from being aspirated into the vacuum tube during suction.

At 2128, the valve 110 can be opened to provide suction through a lumen of the catheter (which may be the same or different than the lumen through which irrigation fluid was provided). At 2130, the valve 110 can be closed to stop suction through the lumen of the catheter through which suction was being provided. In some configurations, injecting irrigation fluid at 2126, providing suction to remove irrigation fluid and/or fragments at 2128, and stopping suction at 2130 can be repeated any suitable number of times. At 2132, the catheter can be removed from the passageway of the patient. In some embodiments, objects can be removed using continuous irrigation without providing suction. For example, using a catheter having at least two passageways (e.g., as shown in FIGS. 9A to 18B and 20A to 27B), providing irrigation through a first passageway can cause objects (e.g., kidney stones) to be transported through another passageway with the irrigation fluid in the absence of suction. In some embodiments, regardless of whether suction is provided in connection with irrigation, irrigation can be provided for any suitable amount of time to remove objects (e.g., kidney stones) from one or more target areas in the subject. For example, irrigation can be provided continuously and/or intermittently for on the order of minutes. In a more particular example, irrigation can be continuously provided for about 5 minutes to about 15 minutes depending on how many objects (e.g., kidney stone fragments) are to be removed, the location of the objects, and whether suction is being used to assist in the removal of the objects.

If a post-inspection of the passageway 132 is to be performed ("YES" at 2134), at 2136, an endoscope can be inserted into the sheath 102 and/or the passageway 134 to inspect whether there are any remaining fragments to be removed. If there are remaining fragments to be removed ("NO" at 2138), 2110 through 2134 can be repeated as necessary until there are no longer fragments to be removed. Otherwise, if the results are acceptable ("YES" at 2138), at 2142 the endoscope (and if present, at 2144, the sheath 102) can be removed from the passageway 134.

At 2146, the passageway 134 can be imaged to inspect for any remaining fragments or other debris and any potential damage (e.g., caused by the procedure). In one non-limiting example, any suitable technique or combination of techniques can be used to image the passageway of the patient. For example, a retrograde pyelogram, an intravenous pyelogram (IVP), and/or any other suitable technique can be performed to provide images of the patient's kidneys 116, the patient's ureter 112, and/or the urinary tract in order to identify problems with the structure or the presence of kidney stones 118, tumors, infection, etc. In some configurations, the retrograde pyelogram or IVP can be performed in association with another suitable imaging technique or combination of techniques, such as an ultrasound, a computed tomography (CT) scan, etc.

At 2148, in some embodiments, a stent can be placed in the passageway 132 of the patient, and the navigation mechanism 106 can be removed at 2150. Note that, in some configurations, the navigation mechanism 106 can be removed at any suitable time, such as prior to providing irrigation fluid (e.g., in configurations where the same lumen is used for the navigation mechanism 106 and irrigation).

FIG. 29A shows an example of a removal device 2200 in accordance with some configurations. As shown in FIG. 29A, the removal device 2200 can include a vacuum tube 2204, a first port 2206 that can be used to receive irrigation fluid, and a second port 2208 that can be used to provide suction to aspirate fluid and/or debris from the passageway of a patient. In some configurations, removal device 2200 can be configured and/or used in a similar manner to removal device 100 described above. Additionally, in some configurations, removal device 2200 can be used with any suitable vacuum tube, such as the vacuum tubes described above in connection with FIGS. 9A to 27B.

FIG. 29B shows an example of irrigation and suction being applied sequentially in accordance with some configurations of the disclosed subject matter. As shown in FIG. 29B, irrigation fluid can be provided (e.g., through the first port of removal device 2200) during time period T1, and suction can be provided to aspirate the irrigation fluid, fragments, etc., during time period T2. This cycle of irrigation and aspiration can be repeated any suitable number of times. Note that the time periods depicted in FIG. 29B are shown for illustration only and are not intended to be drawn to scale.

FIG. 29C shows an example of irrigation and suction being applied simultaneously in accordance with some configurations of the disclosed subject matter. As shown in FIG. 29C, irrigation fluid can be provided (e.g., through the first port of removal device 2200) during time periods T1 and T2, and suction can be provided to aspirate the irrigation fluid, fragments, etc., during time period T2. This cycle of irrigation and aspiration can be repeated any suitable number of times. Note that the time periods depicted in FIG. 29C are shown for illustration only and are not intended to be drawn to scale. Although not shown in FIGS. 29A to 29C, as described above in connection with FIG. 28A, irrigation can be provided continuously (e.g., during the time between time periods T2 and T3 in FIG. 29C) with or without the use of suction.

It should be noted that the removal device 100 may be utilized in the manner described herein without fracturing the kidney stone(s) 118. In particular, the kidney stone(s) may be removed directly so long as they are sized to pass through the removal device 100. The removal device 100 described herein is capable of removing debris having varying sizes. For example, the removal device 100 is designed to remove debris that are characterized as particles of dust (e.g., about 0.001 µm to about 10,000 µm).

The removal device 100 is also designed to remove small, medium, and large kidney stones or other debris. For example, in one configuration, the removal device 100 is designed to remove kidney stones having an approximate diameter of between about 0.0001 mm to about 8 mm. In a different configuration, the removal device 100 is designed to remove kidney stones having an approximate diameter of between about 0.1 mm to about 6 mm. In a different configuration, the removal device 100 is designed to remove kidney stones having an approximate diameter of between about 1 mm to about 5 mm. In still a different configuration, the removal device 100 is designed to remove kidney stones having an approximate diameter of between about 2 mm to about 4 mm. It should be noted that, in one configuration, the removal device 100 described herein is designed to be utilized as described and does not utilize the working channel of a device (i.e., a ureteroscope).

In a further configuration, the removal device 100 is designed for other medical uses, such as, to treat bladder stones and for use with other less invasive procedures, such as percutaneous stone removal, laparoscopic procedures, spine procedures, arthroscopic surgery, and microsurgery (e.g., to treat knee, ankle, foot, and hand issues). The removal device 100 may also be used to remove dead tissue, masses, and other debris. In a further configuration, the removal device 100 is used in a biopsy procedure.

The removal device 100 may be utilized in conjunction with visualization mechanisms including with, for example, fluoroscopy, ultrasound, computerized tomography (CT) scans, and magnetic resonance imaging. One or more portions of the removal device 100 may further comprise one or more radio opaque markers (not shown) and/or radio opaque materials to assist in inserting, positioning, and/or removing the removal device 100. For example, a radio opaque marker may be disposed adjacent an end of the vacuum tube 104 and/or navigation mechanism 106 to assist in the positioning thereof. The marker may be visible to a physician under X-ray, fluoroscopy, or other visual aids. The removal device 100 may include one or more radio opaque markers on other portions thereof, including on the sheath 102, the introducer core 108, or other portions thereof. In use, the physician may use the mark(s), for example, to facilitate placement of the removal device 100 in the patient.

In one particular configuration, the removal device 100 is used in conjunction with fluoroscopy. In another configuration, the removal device 100 is used in conjunction with a cystoscope, miniature camera, or other visualization device. In this configuration, the removal device 100 is not inserted into or utilized by the working channel of the cystoscope. Rather, the cystoscope should have a relatively small diameter (e.g., less than about 3 mm) and the removal device 100 is used in conjunction (separately) therewith or designed as a system with direct visualization and the removal device. A navigation mechanism 106 may optionally be used in this configuration to guide the cystoscope and/or the removal device 100 to the desired location.

One or more portions of the removal device 100 including the sheath 102, the vacuum tube 104, the introducer core 108, and/or the navigation mechanism 106 may include a hydrophilic or hydrophobic coating and/or may comprise a hydrophilic or hydrophobic material. In some configurations, the vacuum tube 104 is coated with a lubricious hydrophilic coating. In one configuration, the coating may be applied to any portion of the sheath 102 to reduce irritation caused by contact with the surrounding tissue in the urinary tract and/or bladder. In another configuration, the coating is applied to portions of the first passageway 142 of the vacuum tube 104 to facilitate debris removal therethrough. In another configuration, the coating is applied to portions of the second passageway 144 of the vacuum tube 104 to facilitate the guidance of the navigation mechanism 106 therethrough. The coating is preferably compatible with the materials used. In one particular configuration, the preferred coating is heparin, although it should be appreciated that other coatings may be utilized. Additionally, one or more portions of the removal device 100 may incorporate a material having the properties as described herein.

In a different configuration, the removal device 100 is used in non-medical applications. In particular, in one configuration, the removal device 100 is used to remove debris from a confined space, such as a hydraulic line, a plumbing line, and/or a petrochemical line, before, during, and/or after repairs to the line(s). The removal device 100 itself may be used to assist in repairing the line(s). Other non-medical uses include the use of the removal device 100 in ventilation systems such as heating and cooling systems and within mechanical or industrial pipes.

Thus, systems and methods are disclosed that are particularly advantageous for addressing the ureter and kidney using an aspirator. For example, some traditional devices treat attempt to meet clinical needs with a separate or dedicated aspirator. However, in the present disclosure, the aspirator may be inserted over a guidewire after a treatment, such as a ureteroscopy with laser, has been performed.

The present invention has been described in terms of one or more preferred embodiments, and it should be appreciated that many equivalents, alternatives, variations, and modifications, aside from those expressly stated, are possible and within the scope of the invention.

What is claimed is:

1. A method for removing an object from a kidney, comprising:
    guiding a flexible tube through a passageway of an in vivo subject, wherein the flexible tube comprises at least a first passageway and a second passageway encompassed by the first passageway, wherein the second passageway is positioned concentrically within the first passageway, the first passageway forming an annular lumen surrounding the second passageway;
    inserting a distal end of the flexible tube into a target region of the kidney;
    infusing liquid through the first passageway substantially continuously into the target region of the kidney during a first period of time;
    initiating suction through the second passageway after the liquid has begun to be infused into the target region of the kidney and simultaneously continuing suction and infusion during a second period of time; and
    aspirating the object through the second passageway with at least a portion of the liquid while the liquid continues to be infused into the target region of the kidney.

2. The method of claim 1, wherein the liquid is infused at a flow rate of at least about 5 milliliters per minute.

3. The method of claim 2, further comprising:
    coupling a bag containing liquid to the second passageway; and
    increasing pressure on the bag to cause the liquid to be infused.

4. The method of claim 1, wherein infusing the liquid comprises infusing the liquid through the first passageway for at least five minutes.

5. The method of claim 1, further comprising:
    causing suction to be provided at the distal end of the second passageway by a suction source coupled to the second passageway; and
    removing another object through the second passageway with at least a second portion of the liquid while the suction is being provided.

6. The method of claim 1, further comprising:
    inserting a sheath into the passageway of the vivo subject;
    inserting a device through the sheath;
    positioning the device adjacent to a second object;
    using the device to break the second object into a plurality of objects including the object; and
    wherein the flexible tube is guided through the sheath.

7. The method of claim 6, wherein the flexible tube is guided through the sheath subsequent to removal of the device.

8. The method of claim 7, wherein the second object is a kidney stone that has a diameter greater than about 10 millimeters and cannot be removed through the first passageway, and the object is a fragment of the kidney stone that has a diameter of less than about 4.33 millimeters.

9. The method of claim 7, wherein the device is a ureteroscope.

10. The method of claim 1, wherein the flexible tube has an external diameter of at least about 11 French.

11. The method of claim 1, wherein the first passageway has a dimension less than a diameter of the object and the second passageway has a circular cross-section having a diameter greater than the diameter of the object.

12. A method for removing an object from a kidney, comprising:
    inserting a sheath into an in vivo passageway of a subject;
    inserting a device through the sheath;
    positioning a distal end of the device within the kidney adjacent to the object;
    using the device to break the object into a plurality of smaller objects;
    removing the device;
    guiding, subsequent to removal of the device, a flexible tube having an external diameter of at least about 11 French through the sheath,
        wherein the flexible tube comprises at least a first passageway and a second passageway encompassed by the first passageway, wherein the second passageway is positioned concentrically within the first passageway, the first passageway forming an annular lumen surrounding the second passageway;
    positioning a distal end of the second passageway adjacent to at least one of the plurality of smaller objects;
    infusing saline solution through the first passageway without suction being applied through the second passageway; and
    applying suction through the second passageway simultaneously with infusing saline solution through the first passageway; and aspirating at least one of the plurality of smaller objects through the second passageway with at least a portion of the saline solution.

13. The method of claim 12, wherein the device is a ureteroscope.

14. The method of claim 12, wherein the first passageway has a dimension less than a diameter of at least one of the plurality of smaller objects.

* * * * *